(12) United States Patent
Okamoto et al.

(10) Patent No.: US 6,835,727 B2
(45) Date of Patent: Dec. 28, 2004

(54) CATHEPSIN CYSTEINE PROTEASE INHIBITORS

(75) Inventors: Osamu Okamoto, Tsukuba (JP); Jean-Pierre Falgueyret, Rigaud (CA); Renata Marcella Oballa, Westmont (CA); Petpiboon Prasit, Pierrefonds (CA); Robert Rydzewski, Newark, CA (US)

(73) Assignees: Merck Frosst Canada & Co., Quebec (CA); Banyu Pharmaceutical Co., Ltd., Tokyo (JP); Axys Pharmaceuticals, Inc., South San Francisco, CA (US)

( * ) Notice: Subject to any disclaimer, the term of this patent is extended or adjusted under 35 U.S.C. 154(b) by 124 days.

(21) Appl. No.: 10/204,772

(22) PCT Filed: Apr. 4, 2001

(86) PCT No.: PCT/US01/11001

§ 371 (c)(1),
(2), (4) Date: Aug. 23, 2002

(87) PCT Pub. No.: WO01/77073

PCT Pub. Date: Oct. 18, 2001

(65) Prior Publication Data

US 2003/0229226 A1 Dec. 11, 2003

Related U.S. Application Data

(60) Provisional application No. 60/195,557, filed on Apr. 6, 2000.

(51) Int. Cl.[7] .................. A61K 31/395; A61K 31/40; C07D 205/02; C07D 207/16; C07D 207/14
(52) U.S. Cl. .................. 514/210; 514/423; 514/424; 514/426; 514/428; 514/408; 548/525; 548/537; 548/557; 548/567; 548/950; 548/952; 548/953; 548/954; 548/566
(58) Field of Search .................. 548/525, 537, 548/557, 567, 950, 952, 953, 954, 566; 546/286, 288, 289; 540/606, 610; 514/212, 210, 329, 344, 426, 428, 423, 424, 408

(56) References Cited

U.S. PATENT DOCUMENTS 4,115,384 A 9/1978 Marsh

FOREIGN PATENT DOCUMENTS

| BE | 641601 | 4/1964 |
|---|---|---|
| DE | 301870 | 11/1917 |
| FR | 1353439 | 4/1963 |
| GB | 994508 | 10/1963 |

OTHER PUBLICATIONS

Srulevitch et al, Acta Pharmaceutica Jugoslavica, 41 (2), pp. 89–106 (1991).*
Chem. Abstracts Online, Registry No. 68253–21–4, Chem. Abstracts 90:91; Franklin et al, Analyst, 103 (1227), pp. 660–662 1978).*
Chem. Abstracts Online, Registry No. 58149–61–4, Chem. Abstracts 84:43108; Ito et al, Bull. of the Chem. Soc. of Japan, 48 (11), pp. 3035–3038 (1975).*
Falgueyret et al., "Novel. Nonpeptidic Cyanamides as Potent and Reversible Inhibitors of Human Cathepsins K and L." J. Med. Chem. (2001). pp. 94–104, vol. 44, No. 1.
Smith et al., "Cathepsin K as a target for the treatment of osteoporosis," Exp. Opin. Ther. Patents, (1999). pp. 683–694, vol. 9. No. 6.
Reid et al.. Synthesis. (1980) pp. 619–621, vol. 8.
Wentrup et al. Tetrahedron, (1970) pp. 4915–4924, vol. 26.
Reid et al., Database Accession No. Brn 127413, (1984), pp. 564–575, vol 12.
Randall et al., Synthetic Communications. (1991), pp. 2025–2032, vol. 21, No. 20.
Funnell et al., Database Accession No. Brn 1363520. "Journal of the Chemistry Society," (1987), pp. 2311–2316.
Verboom et al., "Chemistry of Pyrrolizines; Reactions With Cyanogen Bromide and Trifluoroacetic Anyhydride." Tetrahedron, (1982), pp. 1831–1835, vol. 38, No. 12.
Ban et al., "Nucleic Acids Symposium Series," Symp. Nucleic Acids Chem. (1984), pp. 101–102, No. 14.

* cited by examiner

Primary Examiner—Bernard Dentz
(74) Attorney, Agent, or Firm—Nicole M. Beeler; Mark R. Daniel

(57) ABSTRACT

This invention relates to a novel class of compounds which are cysteine protease inhibitors, including but not limited to, inhibitors of Cathepsins K and L. These compounds are useful for treating diseases in which inhibition of bone resorption is indicated, such as osteoporosis.

16 Claims, No Drawings

CATHEPSIN CYSTEINE PROTEASE INHIBITORS

This application is a 371 of PCT/US01/11001 filed Apr. 4, 2001, which claims priority from Provisional Application 60/195,557 filed Apr. 6, 2000.

BACKGROUND OF THE INVENTION

A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. One of the most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Osteoporosis is characterized by progressive loss of bone architecture and mineralization leading to the loss in bone strength and an increased fracture rate. The skeleton is constantly being remodeled by a balance between osteoblasts that lay down new bone and osteoclasts that breakdown, or resorb, bone. In some disease conditions and advancing age the balance between bone formation and resorption is disrupted; bone is removed at a faster rate. Such a prolonged imbalance of resorption over formation leads to weaker bone structure and a higher risk of fractures.

Bone resorption is primarily performed by osteoclasts, which are multinuclear giant cells. Osteoclasts resorb bone by forming an initial cellular attachment to bone tissue, followed by the formation of an extracellular compartment or lacunae. The lacunae are maintained at a low pH by a proton-ATP pump. The acidified environment in the lacunae allows for initial demineralization of bone followed by the degradation of bone proteins or collagen by proteases such as cysteine proteases. See Delaisse, J. M. et al., 1980, Biochem J 192:365–368; Delaisse, J. et al., 1984, Biochem Biophys Res Commun:441–447; Delaisse, J. M. et al., 1987, Bone 8:305–313, which are hereby incorporated by reference in their entirety. Collagen constitutes 95% of the organic matrix of bone. Therefore, proteases involved in collagen degradation are an essential component of bone turnover, and as a consequence, the development and progression of osteoporosis.

Cathepsins belong to the papain superfamily of cysteine proteases. These proteases function in the normal physiological as well as pathological degradation of connective tissue. Cathepsins play a major role in intracellular protein degradation and turnover and remodeling. To date, a number of cathepsin have been identified and sequenced from a number of sources. These cathepsins are naturally found in a wide variety of tissues. For example, cathepsin B, F, H, L, K, S, W, and Z have been cloned. Cathepsin K (which is also known by the abbreviation cat K) is also known as cathepsin O and cathepsin O2. See PCT Application WO 96/13523, Khepri Pharmaceuticals, Inc., published May 9, 1996, which is hereby incorporated by reference in its entirety. Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immunbe responses, including, but not limited to, rejection of organ transplants or tissue grafts.

Cysteine protease inhibitors such as E-64 (trans-epoxysuccinyl-L-leucylamide-(4-guanidino) butane) are known to be effective in inhibiting bone resorption. See Delaisse, J. M. et al., 1987, Bone 8:305–313, which is hereby incorporated by reference in its entirety. Recently, cathepsin K was cloned and found specifically expressed in osteoclasts See Tezuka, K. et al., 1994, J Biol Chem 269:1106–1109; Shi, G. P. et al., 1995, FEBS Lett 357:129–134; Bromme, D. and Okamoto, K., 1995, Biol Chem Hoppe Seyler 376:379–384; Bromme, D. et al., 1996, J Biol Chem 271:2126–2132; Drake, F. H. et al., 1996, J Biol Chem 271:12511–12516, which are hereby incorporated by reference in their entirety. Concurrent to the cloning, the autosomal recessive disorder, pycnodysostosis, characterized by an osteopetrotic phenotype with a decrease in bone resorption, was mapped to mutations present in the cathepsin K gene. To date, all mutations identified in the cathepsin K gene are known to result in inactive protein. See Gelb, B. D. et al., 1996, Science 273:1236–1238; Johnson, M. R. et al., 1996, Genotie Res 6:1050–1055, which are hereby incorporated by reference in their entirety. Therefore, it appears that cathepsin K is involved in osteoclast mediated bone resorption.

Cathepsin K is synthesized as a 37 kDa pre-pro enzyme, which is localized to the lysosomal compartment and where it is presumably autoactivated to the mature 27 kDa enzyme at low pH. See McQueney, M. S. et al., 1997, J Biol Chem 272:13955–13960; Littlewood-Evans, A. et al., 1997, Bone 20:81–86, which are hereby incorporated by reference in their entirety. Cathepsin K is most closely related to cathepsin S having 56% sequence identity at the amino acid level. The $S_2P_2$ substrate specificity of cathepsin K is similar to that of cathepsin S with a preference in the P1 and P2 positions for a positively charged residue such as arginine, and a hydrophobic residue such as phenylalanine or leucine, respectively. See Bromme, D. et al., 1996, J Biol Chem 271: 2126–2132; Bossard, M. J. et al., 1996, J Biol Chem 271:12517–12524, which are hereby incorporated by reference in their entirety. Cathepsin K is active at a broad pH range with significant activity between pH 4–8, thus allowing for good catalytic activity in the resorption lacunae of osteoclasts where the pH is about 4–5.

Human type I collagen, the major collagen in bone is a good substrate for cathepsin K. See Kafienah, W., et al., 1998, Biochem J 331:727–732, which is hereby incorporated by reference in its entirety. In vitro experiments using antisense oligonucleotides to cathepsin K, have shown diminished bone resorption in vitro, which is probably due to a reduction in translation of cathepsin K mRNA. See Inui, T., et al., 1997, *J Biol Chem* 272:8109–8112, which is hereby incorporated by reference in its entirety. The crystal structure of cathepsin K has been resolved. See McGrath, M. E., et al., 1997, *Nat Struct Biol* 4:105–109; Zhao, B., et al., 1997, *Nat Struct Biol* 4: 109–11, which are hereby incorporated by reference in their entirety. Also, selective peptide based inhibitors of cathepsin K have been developed See Bromme, D., et al., 1996, *Biochem J* 315:85–89; Thompson, S. K., et al., 1997, *Proc Natl Acad Sci USA* 94:14249–14254, which are hereby incorporated by reference in their entirety. Accordingly, inhibitors of Cathepsin K can reduce bone resorption. Such inhibitors would be useful in treating disorders involving bone resorption, such as osteoporosis.

Compounds of the instant invention are useful as inhibitors of cathepsins. More particularly, the compounds of the instant invention are useful as inhibitors of Cathepsins K and L.

It is therefore an object of the invention to provide compounds which inhibit cathepsin activity in a mammal in need thereof.

It is another object of the invention to provide compounds which are useful for treating and/or preventing bone loss in a mammal in need thereof.

It is another object of the invention to provide compounds which are useful to reduce bone loss in a mammal in need thereof.

It is another object of the invention to provide compounds which are useful for treating and/or preventing bone fractures in a mammal in need thereof.

It is another object of the invention to provide compounds which are useful for treating and/or preventing osteoporosis in a mammal in need thereof.

It is another object of the invention to provide compounds which are useful for treating and/or preventing cathepsin dependent conditions or disease states in a mammal in need thereof.

SUMMARY OF THE INVENTION

The present invention relates to compounds of the following chemical formula:

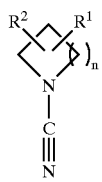

wherein $R^1$ and $R^2$ are each independently selected from the group consisting of hydrogen, alkyl, oxo, —(CH$_2$)$_p$—NH—S(O)$_2$—R$^3$, —(CH$_2$)$_p$—NH—CO—R$^4$, —C(O)$_2$R$^6$, —(CH$_2$)$_p$OR$^5$, —OR$^6$, —(CH$_2$)$_p$NR$^7$R$^8$, —CN, —NH(CH$_2$)$_p$R$^3$, —(CH$_2$)$_p$R$^3$, —R$^3$, —C(O)NHR$^6$ and —C(O)NR$^6$; or $R^1$ and $R^2$ can be joined together to form a system selected from the group consisting of aryl, cycloalkyl and heterocycloalkyl;

$R^3$ is selected from the group consisting of aryl, arylalkyl, cycloalkyl, and heterocycloalkyl, wherein said aryl, arylalkyl and cycloalkyl groups are either unsubstituted or substituted with 1, 2 or 3 halogen atoms;

$R^4$ is selected from the group consisting of aryl, cycloalkyl, heterocycloalkyl, biaryl, CH(R$^{10}$)—NHC(O)$_2$R$^3$, OR$^5$, (CH$_2$)$_p$R$^9$, (CH$_2$)$_p$(R$^9$)$_q$, wherein said aryl, cycloalkyl, heterocycloalkyl and biaryl, groups are either unsubstituted or substituted with 1, 2 or 3 halogen atoms;

$R^5$ is selected from the group consisting of alkyl, alkenyl, alkynyl, and (CH$_2$)$_p$R$^9$;

$R^6$ is selected from the group consisting of hydrogen, alkyl, alkenyl, alkynyl, and CH(R$^{10}$)—NHC(O)$_2$R$^3$;

$R^7$ and $R^8$ are each independently selected from the group consisting of hydrogen, alkyl, alkenyl, alkynyl, and —(CH$_2$)$_p$R$^3$; or $R^7$ and $R^8$ are joined together to form a system selected from the group consisting of aryl and heterocycloalkyl;

$R^9$ is selected from the group consisting of aryl, cycloalkyl and heterocycloalkyl;

$R^{10}$ is selected from the group consisting of the side chains of the naturally occurring amino acids or unnaturally occurring amino acids;

each n is independently an integer from zero to four;

each p is independently an integer from zero to six;

each q is independently an integer from zero to four;

and the pharmaceutically acceptable salts thereof.

The present invention also relate to pharmaceutical compositions comprising the compounds of the present invention and a pharmaceutically acceptable carrier.

The present invention also relates to methods for making the pharmaceutical compositions of the present invention.

The present invention also relates to methods of inhibiting cathepsin activity and/or treating cathepsin dependent conditions in a mammal in need thereof comprising administering to the mammal the compounds and pharmaceutical compositions of the present invention.

The present invention also relates to methods of treating, preventing and/or reducing bone loss in a mammal in need thereof comprising administering to the mammal the compounds and pharmaceutical compositions of the present invention.

The present invention also relates to methods of inhibiting treating and/or preventing osteoporosis in a mammal in need thereof comprising administering to the mammal the compounds and pharmaceutical compositions of the present invention.

The present invention also relates to methods of reducing bone loss in a mammal in need thereof comprising administering to the mammal the compounds and pharmaceutical compositions of the present invention.

The present invention also relates to methods of treating and/or preventing bone fractures in a mammal in need thereof comprising administering to the mammal the compounds and pharmaceutical compositions of the present invention.

The present invention relates to the use of the compounds and pharmaceutical compositions of the present invention for the preparation of a medicament for treating or preventing bone loss in a mammal in need thereof.

The present invention relates to pharmaceutical compositions useful for treating or preventing bone loss in a mammal comprising a pharmaceutically effective amount of compounds of the present invention in association with pharmaceutically acceptable carriers.

DETAILED DESCRIPTION OF THE INVENTION

The present invention relates to compounds of the following chemical formula:

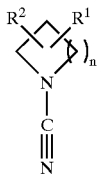

wherein

R$^1$ and R$^2$ are each independently selected from the group consisting of hydrogen, alkyl, oxo, —(CH$_2$)$_p$—NH—S(O)$_2$—R$^3$, —(CH$_2$)$_p$—NH—CO—R$^4$, —C(O)$_2$R$^6$, —(CH$_2$)$_p$OR$^5$, —OR$^6$, (CH$_2$)$_p$NR$^7$R$^8$, —CN, —NH(CH$_2$)$_p$R$^3$, —(CH$_2$)$_p$R$^3$, —R$^3$, —C(O)NHR$^6$ and —C(O)NR$^{6;\ or\ R1}$ and R$^2$ can be joined together to form a system selected from the group consisting of aryl, cycloalkyl and heterocycloalkyl;

R$^3$ is selected from the group consisting of aryl, arylalkyl, cycloalkyl, and heterocycloalkyl, wherein said aryl, arylalkyl and cycloalkyl groups are either unsubstituted or substituted with 1, 2 or 3 halogen atoms;

R$^4$ is selected from the group consisting of aryl, cycloalkyl, heterocycloalkyl, biaryl, CH(R$^{10}$)—NHC(O)$_2$R$^3$, OR$^5$, (CH$_2$)$_p$R$^9$, (CH$_2$)$_p$(R$^9$)$_q$, wherein said aryl, cycloalkyl, heterocycloalkyl and biaryl, groups are either unsubstituted or substituted with 1, 2 or 3 halogen atoms;

R$^5$ is selected from the group consisting of alkyl, alkenyl, alkynyl, and (CH$_2$)$_p$R$^9$;

R$^6$ is selected from the group consisting of hydrogen, alkyl, alkenyl, alkynyl, and CH(R$^{10}$)—NHC(O)$_2$R$^3$;

R$^7$ and R$^8$ are each independently selected from the group consisting of hydrogen, alkyl, alkenyl, alkynyl, and —(CH$_2$)$_p$R$^3$; or R$^7$ and R$^8$ are joined together to form a system selected from the group consisting of aryl and heterocycloalkyl;

R$^9$ is selected from the group consisting of aryl, cycloalkyl and heterocycloalkyl;

R$^{10}$ is selected from the group consisting of the side chains of the naturally occurring amino acids or unnaturally occurring amino acids;

each n is independently an integer from zero to four;
each p is independently an integer from zero to six;
each q is independently an integer from zero to four;
and the pharmaceutically acceptable salts thereof.

In the compounds of the present invention, R$^1$ and R$^2$ are each independently and preferably selected from the group consisting of: hydrogen, —(CH$_2$)$_p$—NH—S(O)$_2$—R$^3$, —(CH$_2$)$_p$—NH—CO—R$^4$, —C(O)$_2$R$^6$, —(CH$_2$)$_p$OR$^5$, —OR$^6$, —CN, —N(CH$_2$)$_p$R$^3$, —(CH$_2$)$_p$R$^3$, and —C(O)NR$^6$; or R$^1$ and R$^2$ can be joined together to form a system selected from the group consisting of aryl, cycloalkyl and heterocycloalkyl.

In the compounds of the present invention, each n is independently and preferably an integer from zero to two.

In the compounds of the present invention, R$^{10}$ is preferably selected from the group consisting of the side chains of leucine and isoleucine.

In the compounds of the present invention, each p is independently and preferably an integer from zero to four.

An embodiment of the invention is a method of inhibiting cathepsin activity in a mammal in need thereof, comprising administering to the mammal a therapeutically effective amount of any of the compounds or any of the above pharmaceutical compositions described above.

A class of the embodiment is the method wherein the cathepsin activity is cathepsin K activity.

A second class of the embodiment is the method wherein the cathepsin activity is cathepsin L activity.

Another embodiment of the invention is a method of treating or preventing cathepsin dependent conditions in a mammal in need thereof, comprising administering to the mammal a therapeutically effective amount of any of the compounds or any of the above pharmaceutical compositions described above.

A class of the embodiment is the method wherein the cathepsin activity is cathepsin K activity.

A second class of the embodiment is the method wherein the cathepsin activity is cathepsin L activity.

Another embodiment of the invention is a method of treating or preventing bone loss in a mammal in need thereof, comprising administering to the mammal a therapeutically effective amount of any of the compounds or any of the above pharmaceutical compositions described above.

Another embodiment of the invention is a method of reducing bone loss in a mammal in need thereof, comprising administering to the mammal a therapeutically effective amount of any of the compounds or any of the above pharmaceutical compositions described above.

Another embodiment of the invention is a method of treating or preventing bone fractures in a mammal in need thereof, comprising administering to the mammal a therapeutically effective amount of any of the compounds or any of the above pharmaceutical compositions described above.

Another embodiment of the invention is a method of treating or preventing osteoporosis in a mammal in need thereof, comprising administering to the mammal a therapeutically effective amount of any of the compounds or any of the above pharmaceutical compositions described above.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

Further exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, and/or disorders related to cathepsin functioning.

The present invention is also directed to combinations of any of the compounds or any of the pharmaceutical compositions described above with one or more agents useful in the prevention or treatment of osteoporosis. For example, the compounds of the instant invention may be effectively administered in combination with effective amounts of other agents such as an organic bisphosphonate or an estrogen receptor modulator. Nonlimiting examples of said organic bisphosphonates include alendronate, clodronate, etidronate, ibandronate, incadronate, minodronate, neridronate, risedronate, piridronate, pamidronate, tiludronate, zoledronate, pharmaceutically acceptable salts or esters thereof, and mixtures thereof. Preferred organic bisphosphonates include alendronate and pharmaceutically acceptable salts and mixtures thereof. Most preferred is alendronate monosodium trihydrate.

The precise dosage of the bisphosphonate will vary with the dosing schedule, the oral potency of the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 $\mu$g/kg body weight and preferably about 10 to about 2000 $\mu$g/kg of body weight.

For human oral compositions comprising alendronate, pharmaceutically acceptable salts thereof, or pharmaceutically acceptable derivatives thereof, a unit dosage typically comprises from about 8.75 mg to about 140 mg of the alendronate compound, on an alendronic acid active weight basis, i.e. on the basis of the corresponding acid.

For use in medicine, the salts of the compounds of this invention refer to non-toxic "pharmaceutically acceptable salts." Other salts may, however, be useful in the preparation of the compounds according to the invention or of their pharmaceutically acceptable salts. When the compounds of the present invention contain a basic group, salts encompassed within the term "pharmaceutically acceptable salts" refer to non-toxic salts which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucaamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The compounds of the present invention can have chiral centers and occur as racemates, racemic mixtures, diastereomeric mixtures, and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs, hydrates and solvates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "bone resorption," as used herein, refers to the process by which osteoclasts degrade bone.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range containing at least one double bond (i.e., —CH═CH$_2$, —CH$_2$CH═CH$_2$, —CH═CHCH$_3$, —CH$_2$CH═C(CH$_3$)$_2$, etc.).

The term "alkynyl" shall mean straight or branched chain alkynes of two to ten total carbon atoms, or any number within this range containing at least one triple bond (i.e., —C≡CH, —CH$_2$C≡H, —C≡CCH$_3$, —CH$_2$C≡CCH$_2$(CH$_3$)$_2$, etc.).

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "cycloalkenyl" shall mean a substituting univalent group derived by conceptual removal of one hydrogen atom from an unsaturated monocyclic hydrocarbon containing a double bond (i.e., cyclopentenyl or cyclohexenyl).

The term "cycloheteroalkyl," as used herein, shall mean a 3- to 8-membered fully saturated heterocyclic ring containing one or two heteroatoms chosen from N, O or S. Examples of cycloheteroalkyl groups include, but are not limited to, oxiranyl, piperidinyl, pyrrolidinyl, azetidinyl, morpholinyl, piperazinyl.

The term "aryl," as used herein, refers to a monocyclic or polycyclic system comprising at least one aromatic ring, wherein the monocylic or polycyclic system contains 0, 1, 2, 3, or 4 heteroatoms chosen from N, O, or S, and wherein the monocylic or polycylic system is either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino-$C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Examples of aryl include, but are not limited to, phenyl, naphthyl, pyridyl, pyrazinyl, pyrimidinyl, imidazolyl, benzimidazolyl, indolyl, thienyl, furyl, dihydrobenzofuryl, benzo(1,3) dioxolane, oxazolyl, isoxazolyl and thiazolyl, which are either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Preferably, the aryl group is unsubstituted, mono-, di-, tri- or tetra-substituted with one to four of the above-named substituents; more preferably, the aryl group is unsubstituted, mono-, di- or tri-substituted with one to three of the above-named substituents; most preferably, the aryl group is unsubstituted, mono- or di-substituted with one to two of the above-named substituents.

Whenever the term "alkyl" or "aryl" or either of their prefix roots appear in a name of a substituent (e.g., aryl $C_{0-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluyl, ethylphenyl, and propylphenyl.

The term "halogen" shall include iodine, bromine, chlorine and fluorine.

The term "oxy" means an oxygen (O) atom. The term "thio" means a sulfur (S) atom. The term "oxo" means =O. The term "oximino" means the =C(H)NOH group.

The term "side chain" refers to the portion of an amino acid that is bonded to the tetrahedral alpha carbon that is not the amino or carboxyl group. Nonlimiting examples of side chains include —$CH_2CH_2CH_2CH_2NH_3$ (lysine) and —$CH_3$ (alanine).

The term "naturally occurring amino acids" refers to the amino acids that include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

The term "unnaturally occurring amino acids" refers to amino acids that have alpha side chains other than those found in the natural amino acids. Nonlimiting examples of unnaturally occurring amino acids include the nitriles of leucine, isoleucine, tryptophan, methionine, phenylalanine, proline, alanine, and valine, spirocycloalkyls (see example below), alkyl and alkenyl groups, halogenated versions of natural amino acid side chains and —$(CH_2)_P R^3$.

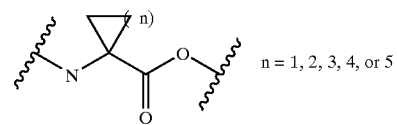

n = 1, 2, 3, 4, or 5

In the compounds of the present invention, $R^1$ and $R^2$ can be taken together with any of the atoms to which they may be attached or are between them to form a 4–6 membered ring system.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The term "protected" and "PG" when used throughout shall refer to α-amino protection or α-carboxyprotection. Examples of α-amino protecting groups include, but are not limited to, benzyloxycarbonyl, t-butoxycarbonyl, 2-(4-biphenylyl)-isopropoxycarbonyl, 9-fluoroenylmethoxycarbonyl, triphenylmethyl and 2-nitrophenylsulphenyl. Examples of α-carboxy protecting groups include, but are not limited to, methyl and ethyl esters, benzyl esters, t-butyl esters and phenyl esters.

The term "unprotected" shall refer to free $NH_2$ or C(O)OH termini.

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "biaryl" as used herein refers to a nonfused (as opposed to a fused), bicyclic ring system. The biarylene system is incorporated into the molecules of the present invention through either one of two connectivity or bonding points. The biarylene system comprises two aromatic ring systems, wherein each of the aromatic ring systems is a 5- or 6-membered aromatic ring system. The biarylene system comprises 0–8 heteroatoms selected from the group consisting of N, O, and S. The biarylene system can be either unsubstituted or substituted with one or more $R^1$ substituents. The two aromatic ring systems of the biarylene system can be the same or different. Nonlimiting examples of biarylene systems useful herein include those selected from the group consisting of

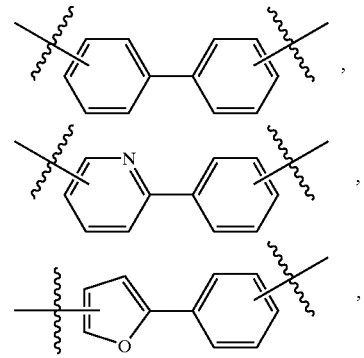

-continued

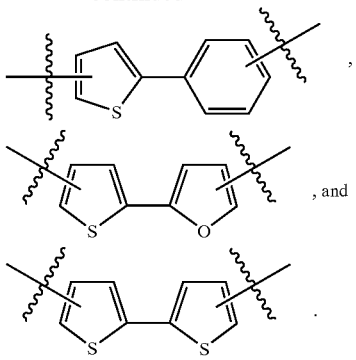
, and

Under standard nonmenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

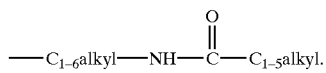

In choosing compounds of the present invention, one of ordinary skill in the art will recognize that the various substituents, i.e. $R^1$, $R^2$, $R^3$, $R^4$, $R^5$, $R^6$, $R^7$, $R^8$, $R^9$, $R^{10}$, n, p and q are to be chosen in conformity with well-known principles of chemical structure connectivity.

The compounds of the present invention are available in racemic form or as individual enantiomers. It is generally preferable to administer the compounds of the present invention structure as enantiomerically pure formulations since most or all of the desired bioactivity resides with a single enantiomer. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The compounds of the present invention can be used in combination with other agents useful for treating cathepsin-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating estrogen-mediated conditions includes in principle any combination with any pharmaceutical composition useful for treating disorders related to estrogen functioning.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixers, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

For purposes of this specification, the following abbreviations have the indicated meanings:

| | |
|---|---|
| $BH_3 \cdot Me_2S$ = | borane-methyl sulfide complex |
| Boc = | t-butyloxycarbonyl |
| $Boc_2O$ = | di-tert-butyl dicarbonate |
| BrCN = | cyanogen bromide |
| $CCl_4$ = | carbon tetrachloride |
| $CH_2Cl_2$ = | methylene chloride |
| $CH_3CN$ = | acetonitrile |
| $CHCl_3$ = | chloroform |
| $Cs_2CO_3$ = | cesium carbonate |
| DMAP = | 4-(dimethylamino)pyridine |
| DMF = | N,N-dimethylformamide |
| DMSO = | dimethylsulfoxide |
| DPPA = | diphenylphosporyl azide |
| EDCI = | 1-(3-dimethylaminopropyl)-3-ethylcarbodiimide hydrochloride |
| $Et_2O$ = | diethyl ether |
| $Et_3N$ = | triethylamine |
| EtOAc = | ethyl acetate |
| EtOH = | ethanol |
| HOAc = | acetic acid |
| mCPBA = | metachloroperbenzoic acid |
| MeOH = | methanol |
| $MgSO_4$ = | magnesium sulfate |
| Ms = | methanesulfonyl = mesyl |
| MsCl = | methanesulfonyl chloride |
| $Na_2NCN$ = | disodium cyanamide |
| $NaBH_4$ = | sodium borohydride |
| NaCN = | sodium cyanide |
| NaH = | sodium hydride |
| $NaHCO_3$ = | sodium hydrogencarbonate |
| $NaN_3$ = | sodium azide |
| NaOH = | sodium hydroxide |
| NBS = | N-bromosuccinimide |
| $NH_3$ = | ammonia |
| $NH_4Cl$ = | ammonium chloride |
| Pd/C = | palladium on carbon |
| rt = | room temperature |
| sat. aq. = | saturated aqueous |
| TFA = | trifluoroacetic acid |
| THF = | tetrahydrofuran |
| tlc = | thin layer chromatography |
| TMSCN = | trimethylsilyl cyanide |
| Me = | methyl |
| Et = | ethyl |
| n-Pr = | normal propyl |
| i-Pr = | isopropyl |
| n-Bu = | normal butyl |

| | |
|---|---|
| i-Bu = | isobutyl |
| s-Bu = | secondary butyl |
| t-Bu = | tertiary butyl |

The novel compounds of the present invention can be prepared according to the following general procedures using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

GENERAL PROCEDURE I

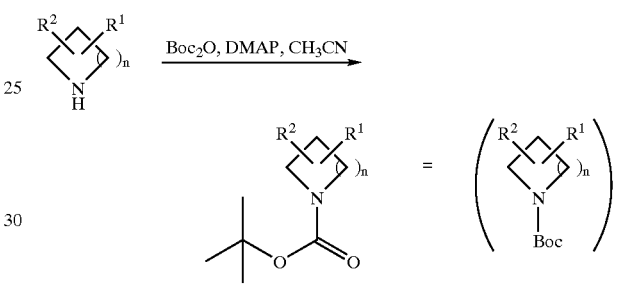

To a stirred solution of the starting amine (1 equiv.) in $CH_3CN$ (~2 mL per mmol of starting amine) was added a solution of DMAP (2 equiv.) in $CH_3CN$ (~0.3 mL per mmol of DMAP) followed by the dropwise addition (over 30 minutes) of $Boc_2O$ (1.2 equiv.) in $CH_3CN$ (~0.3 mL per mmol of $Boc_2O$). The resultant solution was stirred at rt until the reaction was complete, as determined by tlc analysis (3 to 24 h). The solution was then diluted with EtOAc, washed with 10% citric acid, $H_2O$ and brine. The organic extract was dried over $MgSO_4$ and concentrated under reduced pressure to afford the desired Boc-protected amine.

To a cold (−5° C.), stirred suspension of bromine (5.5 mL, 1 equiv.) in $H_2O$ (15 mL) was added, dropwise over 30 minutes, a solution of sodium cyanide (5.0 g, 1 equiv.) in $H_2O$ (15 mL). The temperature of the reaction mixture during the addition of sodium cyanide was maintained at −5 to 5° C. The resultant suspension was stirred an additional 10 minutes and was then extracted with $CH_2Cl_2$ (3×33.3 mL). The resultant solution of BrCN (1 M in $CH_2Cl_2$) was stored over $CaCl_2$ at 4° C.

GENERAL PROCEDURE 3

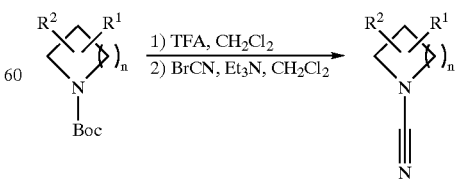

To a stirred solution of the Boc-protected amine (1 equiv.) in $CH_2Cl_2$ (~1 mL per mmol of the amine) was added TFA (16 equiv.). The solution was stirred at rt for 0.5 h and the CH$_2$Cl$_2$/TFA solvent was removed under reduced pressure. The residue was diluted with CH$_2$Cl$_2$ and the solvent was removed once again under reduced pressure (repeated 2×).

The resultant amine was dissolved in CH$_2$Cl$_2$ (~5 mL per mmol of amine) and cooled to 0° C. To this cold solution was added Et$_3$N (1.5 equiv.) followed by a solution of BrCN in CH$_2$Cl$_2$ (prepared as described in general procedure 2, 1 M, 1.1 to 5 equiv.). The resultant reaction mixture was stirred at 0° C. for 1 h. The solution was warmed to rt, diluted with EtOAc and washed with H$_2$O and brine. The organic extract was dried (MgSO$_4$), concentrated under reduced pressure and the resultant residue was purified by flash chromatography to afford the desired cyanamide.

GENERAL PROCEDURE 4

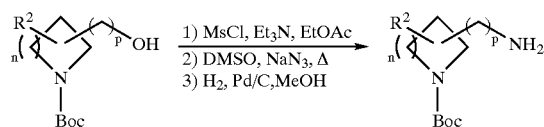

To a cold (0° C.), stirred solution of the primary alcohol (1 equiv.) in EtOAc or THF (3 to 20 mL per mmol of alcohol) was added Et$_3$N (1.5 to 2 equiv.) followed by MsCl (1.2 to 1.5 equiv.). The resultant suspension was stirred at 0° C. for 0.5 to 1 h. The undissolved material (Et$_3$N.HCl) was filtered off and washed with EtOAc. The organic filtrate was concentrated under reduced pressure to afford an oil. This crude oil (mesylate) was dissolved in DMSO (2 mL per mmol of starting alcohol) and NaN$_3$ (1.5 to 2 equiv.) was added. The resultant reaction mixture was stirred at 70–100° C. for 2–5 hours. The reaction mixture was then poured into H$_2$O and extracted with Et$_2$O (4×). The combined organic extracts were washed with H$_2$O and brine, dried over MgSO$_4$ and concentrated under reduced pressure to afford the desired azide which was either purified by flash chromatography or used crude in the next reaction.

To a stirred solution of the azide (1 equiv.) in MeOH (2–3 mL per mmol of azide) was added 5 to 10% Pd on carbon (5 to 10% of azide weight). The solution was evacuated, placed under a H$_2$ atmosphere (1 atm) and stirred at rt for 1 day. The suspension was then filtered through celite and washed with MeOH. The filtrate was concentrated under reduced pressure to afford the desired primary amine.

GENERAL PROCEDURE 5

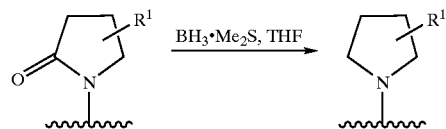

To a cold (0° C.), stirred solution of amide (1 equiv.) in THF (0.5 to 1 mL per mmol of amide) was added, dropwise, a solution of BH$_3$·Me$_2$S in THF (2 M, 2 equiv.). The resultant mixture was then heated to reflux for 1 to 2 h. The reaction was cooled to rt and MeOH was added (0.2 mL per mmol of amide). The solution was concentrated under reduced pressure and the residue was then dissolved in EtOAc, washed with sat. aq. NH$_4$Cl (2×) and brine. The organic extract was dried (MgSO$_4$) and concentrated under reduced pressure to afford the desired amine which was purified using flash chromatography.

GENERAL PROCEDURE 6

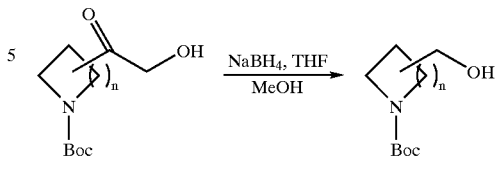

To a refluxing suspension of the ester (1 equiv.) and NaBH$_4$ (2 equiv.) in THF (1 mL per mmol of ester) was added, dropwise, MeOH (0.2 mL per mmol of ester). After the addition of MeOH, the resulting mixture was refluxed for 1 h. The mixture was then poured into 10% citric acid and extracted with EtOAc (3×). The combined organic extracts were washed with H$_2$O and brine, dried (MgSO$_4$) and concentrated under reduced pressure. The resultant oil was purified using flash chromatography to afford the desired alcohol.

GENERAL PROCEDURE 7

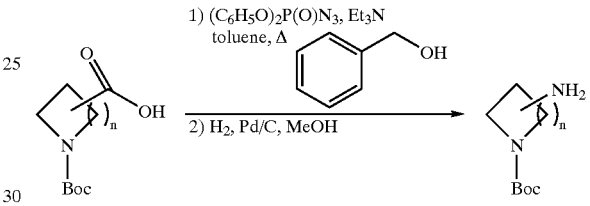

To a stirred solution of the acid (1 equiv.) and Et$_3$N (1.2 equiv.) in toluene (2.8 mL per mmol of acid) was added DPPA ((C$_6$H$_5$O)$_2$P(O)N$_3$, 1.1 equiv.). After stirring at rt for 10 minutes, the mixture was refluxed for 1 h. To this refluxing mixture was added benzyl alcohol (2 equiv.) and the refluxing was continued for 14 h. The resultant mixture was poured into 1 N aq. NaOH and extracted with Et$_2$O (3×). The combined organic extracts were washed successively with H$_{12}$O, 10% citric acid, H$_2$O and brine. The organic extracts were dried (MgSO$_4$), concentrated under reduced pressure and the residue was purified by flash chromatography to afford the benzyl carbamate intermediate.

To a stirred solution of the benzyl carbamate intermediate (1 equiv.) in MeOH (3 mL per mmol of benzyl carbamate) was added 10% palladium on carbon (10%). The solution was evacuated, placed under a H$_2$ atmosphere (35 atm) and shaken for 5 h. The suspension was then filtered through celite and washed with MeOH. The filtrate was concentrated under reduced pressure to afford the desired amine.

GENERAL PROCEDURE 8

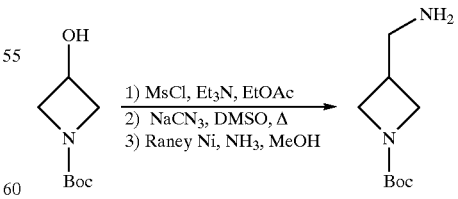

To a cold (0° C.), stirred solution of the primary alcohol (1 equiv.) in EtOAc (1.5 mL per mmol of alcohol) was added Et$_3$N (1.3 equiv.) followed by MsCl (1.2 equiv.). The resultant suspension was stirred at 0° C. for 1 h. The undissolved material (Et$_3$N—HCl) was filtered off and washed with EtOAc. The organic filtrate was concentrated under reduced pressure to afford an oil. This crude oil (mesylate) was dissolved in DMSO (0.7 mL per mmol of starting alcohol) and NaCN (2 equiv.) was added. The resultant reaction mixture was stirred at 130° C. for 2 days. The reaction mixture was then poured into H$_2$O and extracted with Et$_2$O (2×). The combined organic extracts were washed with H$_2$O and brine, dried over MgSO$_4$ and concentrated under reduced pressure to afford the desired azide which was purified by flash chromatography.

To a stirred solution of the azide (1 equiv.) in NH$_3$/MeOEH (2 M, 4 mL per mmol of azide) was added raney nickel (~0.25 mL per mmol of azide). The mixture was evacuated, placed under a H$_2$ atmosphere (40 atm) and shaken at it for 3.5 h. The suspension was then filtered through celite and washed with MeOH. The filtrate was concentrated under reduced pressure to afford the desired primary amine.

GENERAL PROCEDURE 9

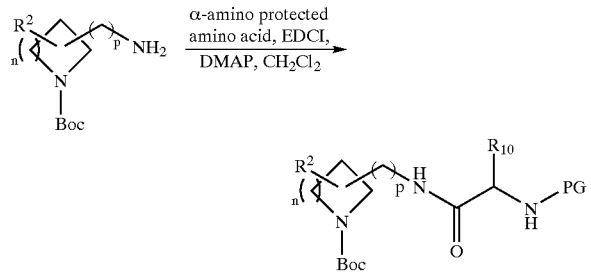

To a stirred solution of the amine (1 equiv.), α-amino protected amino acid (1 equiv.) and EDCI (1.1 equiv.) in CH$_2$Cl$_2$ (5 mL per mmol of amine) was added DMAP (0.5 equiv.). The resultant mixture was stirred at rt for 16 h. The mixture was then diluted with EtOAc and washed successively with 10% citric acid, H$_2$O and brine. The organic extract was dried (MgSO$_4$) and concentrated under reduced pressure. The residue was purified by flash chromatography to afford the desired coupled product.

GENERAL PROCEDURE 10

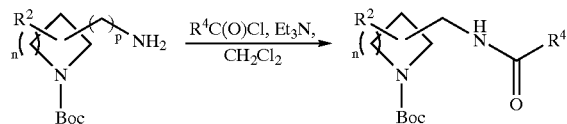

To a stirred solution of the amine (1 equiv.) and Et$_3$N (1.5 equiv.) in CH$_2$Cl$_2$ (10 mL per mmol of amine) was added the acid chloride (R$^4$C(O)Cl, 1.1 equiv.). The resultant mixture was stirred at rt for 10 minutes. The mixture was then diluted with EtOAc and washed successively with 10% citric acid, H$_2$O and brine. The organic extract was dried (MgSO$_4$) and concentrated under reduced pressure. The residue was purified by flash chromatography to afford the desired coupled product.

GENERAL PROCEDURE 11

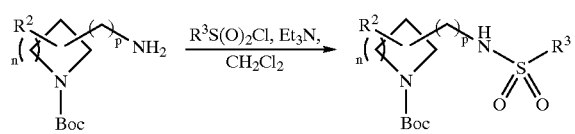

To a cold (0° C.), stirred solution of the amine (1 equiv.) and Et$_3$N (1.5 equiv.) in CH$_2$Cl$_2$ (10 mL per mmol of amine) was added the arylsulfonyl chloride (R$^3$S(O)$_2$Cl, 1.1 equiv.). The resultant mixture was stirred at rt for 16 h. The mixture was then diluted with EtOAc and washed successively with 10% citric acid, H$_2$O and brine. The organic extract was dried (MgSO$_4$) and concentrated under reduced pressure. The residue was purified by flash chromatography to afford the desired sulfonamide.

GENERAL PROCEDURE 12

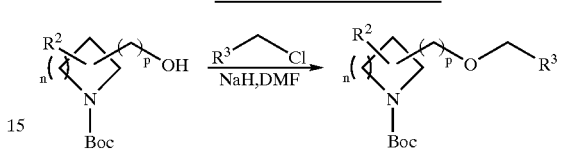

To a cold (0° C.), stirred solution of the alcohol (1 equiv.) in DMF (10 mL per mmol of alcohol) was added NaH (1.5 equiv.). The suspension was stirred at 0° C. for 40 minutes followed by the addition of the aryl chloride (R$^3$CH$_2$Cl, 2 equiv.). The suspension was warmed to rt and stirred for 6 h. MeOH was added followed by sat. aq. NH$_4$Cl. The aqueous phase was extracted with EtOAc (3×) and the combined organic extracts were washed with brine, dried (MgSO$_4$) and concentrated under reduced pressure. The residue was purified by flash chromatography to afford the desired benzyl ether.

SCHEME 1

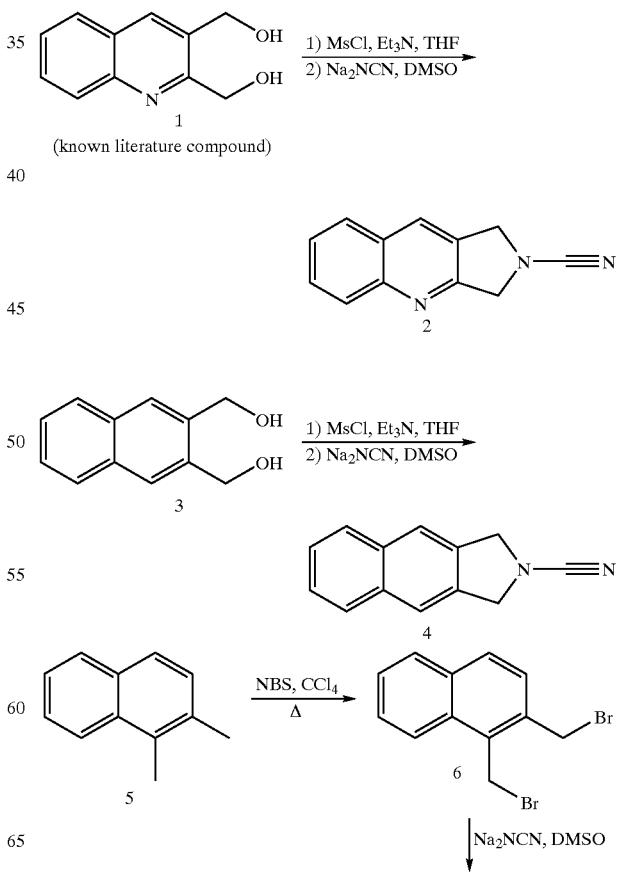

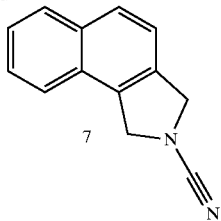

To a cold (0° C.), stirred solution of the diol 1(208 mg, 1 equiv.) ([1].

Rao, A. V. R.; Yadav, J. S.; Valluri, M. *Tetrahedron Lett.* 1994, 35, 3616) in THF (24 mL) was added Et$_3$N (460 uL, 3 equiv.) followed by MsCl (213 uL, 2.5 equiv.). The resultant suspension was stirred at rt for 1 h. The suspension was then diluted with EtOAc and the mixture was washed with 10% citric acid, H$_2$O, sat. aq. NaHCO$_3$ and brine. The combined aqueous washings were back extracted with EtOAc (2×) and the combined organic extracts were dried over MgSO$_4$ and concentrated under reduced pressure to afford the desired dimesylate which was used immediately in the next reaction. The crude dimesylate (420 mg, 1 equiv.) was dissolved in DMSO (10 mL) and Na$_2$NCN (189 mg, 2 equiv.) was added. The dark red solution was stirred at rt for 2 h at which point H$_2$O was added. The aqueous phase was extracted with EtOAc (3×) and the combined organic extracts were washed with H$_2$O and brine, dried over MgSO$_4$ and concentrated under reduced pressure. The resultant residue was purified by flash chromatography (40% EtOAc in hexane) to afford 2-cyano-2,3-dihydro-1H-pyrrolo[3,4-b]quinoline (2).

$^1$H NMR (400 MHz, acetone-d6): δ 5.93 (s, 1H), 8.02 (d, J=8.6 Hz, 1H), 7.96 (d, J=7.4 Hz, 1H), 7.76 (t, J=7.7 Hz, 1H), 7.60 (t, J=7.5 Hz, 1H), 5.00 (s, 2H), 4.86 (s, 2H); m/z (+APCI): 196.0 (M+1)$^+$.

To a cold (0° C.), stirred solution of the diol (3) (307 mg, 1 equiv.) in THF (25 mL) was added Et$_3$N (680 uL, 3 equiv.) followed by MsCl (320 uL, 2.5 equiv.). The resultant suspension was stirred at rt for 0.5 h. The suspension was then diluted with EtOAc and the mixture was washed with 10% citric acid, H$_2$O, sat. aq. NaHCO$_3$, H$_2$O and brine. The organic extract was dried over MgSO$_4$ and concentrated under reduced pressure to afford the desired dimesylate which was used immediately in the next reaction. The crude dimesylate was dissolved in DMSO (16 mL) and Na$_2$NCN (280 mg, 2 equiv.) was added. The dark red suspension was stirred at rt for 1 h at which point the mixture was poured into H$_2$O. The aqueous phase was extracted with Et$_2$O (3×) and the combined organic extracts were washed with H$_2$O and brine, dried over MgSO$_4$ and concentrated under reduced pressure. The resultant residue was purified by flash chromatography (gradient elution: 20% EtOAc in hexane to 50% EtOAc in hexane) to afford 2-cyano-2,3-dihydro-1H-benzo[f]isoindole (4).

$^1$H NMR (300 MHz, acetone-d6): δ 7.89 (m, 2H), 7.85 (s, 2H), 7.49 (m, 2H), 4.60 (s, 4H); m/z (+APCI): 195.2 (M+1)$^+$.

To a stirred solution of 1,2-dimethylnaphthalene (5) (1.56 g, 1 equiv.) in CCl$_4$ (10 mL) was added NBS (3.56 g, 2 equiv.). The reaction mixture was then refluxed for 1 h. After cooling to rt, the mixture was filtered and washed with CHCl$_3$. The filtrate was washed with H$_2$O and brine, dried over MgSO$_4$ and concentrated under reduced pressure to yield a crude solid. This solid was washed with a small portion of toluene/CHCl$_3$ to yield the purified dibromide (6). To a suspension of Na$_2$NCN (516 mg, 2 equiv.) in DMSO (30 mL) was added the dibromide (6) (924 mg, 1 equiv.). The suspension was stirred at rt for 1 h at which point the mixture was poured into H$_2$O. The aqueous phase was extracted with Et$_2$O (3×) and the combined organic extracts were washed with H$_2$O and brine, dried over MgSO$_4$ and concentrated under reduced pressure. The resultant residue was purified by flash chromatography (gradient elution: 10% EtOAc in hexane to 20% EtOAc in hexane) to afford the solid 2-cyano-2,3-dihydro-1H-benzo[e]isoindole (7).

$^1$H NMR (400 MHz, acetone-d6): δ 7.98 (d, 1H), 7.95 (d, 1H), 7.76 (d, 1H), 7.58 (m, 2H), 7.47 (d, 1H), 5.17 (s, 2H), 4.96 (s, 2H).

SCHEME 2

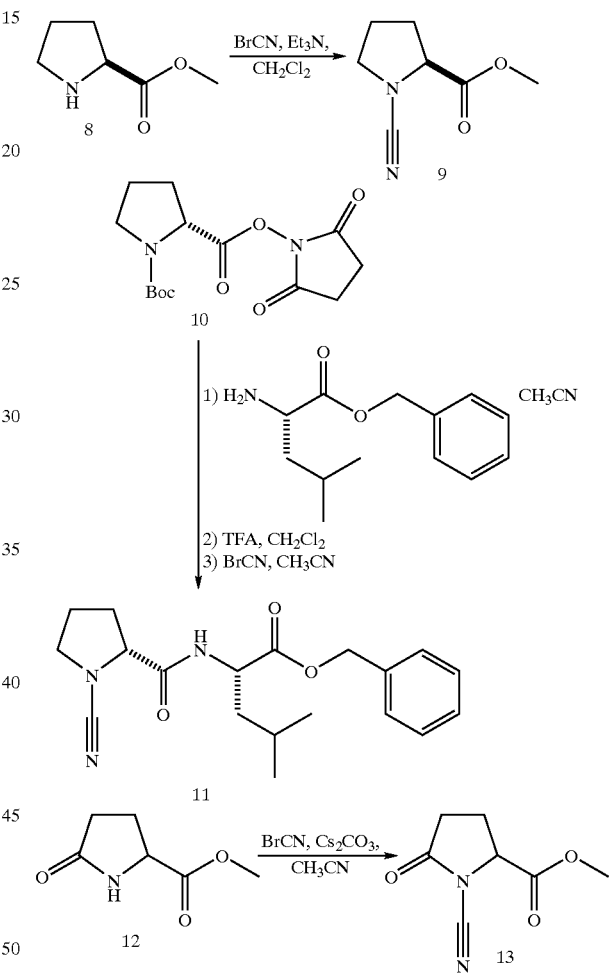

Following general procedure 3 (second reaction), the amine (3) (167 mg, 1 equiv.) in CH$_2$Cl$_2$ (10 mL) was treated with Et$_3$N (0.35 mL, 2.5 equiv.) and BrCN (1 mL of a 1 M solution in CH$_2$Cl$_2$, 1 equiv.) to afford, after work-up, the desired methyl 1-cyano-2-pyrrolidinecarboxylate (9).

$^1$H NMR (400 MHz, acetone-d6): δ 4.30 (m, 1H), 3.75 (s, 3H), 3.50 (m, 2H), 2.29 (m, 1H), 1.96 (m, 3H).

N-(t-Butoxycarbamoyl)-(D)-proline N-hydroxysuccinimide ester (10) (1.25 g, 4.0 mmol) and (L)-leucine benzyl ester (0.885 g, 4.0 mmol) were stirred at ambient temperature in acetonitrile (10 mL) for 14 h. The solvent was evaporated and the residue was partitioned between ethyl acetate and water. The organic phase was separated and washed with 1N HCl, saturated NaHCO$_3$, and saturated NaCl. After drying over anhydrous MgSO$_4$, evaporation of solvent gave N-(t-butyoxycarbamoyl)-(D)-prolylleucine benzyl ester as a colorless oil. N-(t-Butoxycarbamoyl)-(D)-prolylleucine benzyl ester (1.38 g, 3.3 mmol) was stirred for one hour at ambient temperature with a 30% (v/v) solution of trifluroacetic acid in dichloromethane (20 mL). The solvent was removed by rotary evaporation and the residue partitioned between ethyl acetate and a 50% (v/v) solution of saturated aq. NaHCO$_3$ and saturated aq. Na$_2$CO$_3$. The organic phase was separated, washed with saturated aq. NaCl, and dried over anhydrous MgSO$_4$. Filtration and solvent evaporation gave (D)-prolylleucine benzyl ester as a white semi-solid.

A mixture of 10 mL diethyl ether, 2 mL water, and 150 mg magnesium carbonate was cooled in an ice bath and 0.83 mL (4.16 mmol) 5M cyanogen bromide in acetonitrile was added with stirring. A solution of (D)-prolyl-leucine benzyl ester (883 mg, 2.77 mmol) in 17 mL diethyl ether was added over the course of 10 minutes. Another 0.20 mL (1.0 mmol) of 5M cyanogen bromide in acetonitrile was then added and the mixture was stirred at room temperature for 30 minutes. The organic phase was decanted and the aqueous phase extracted twice with diethyl ether. The combined ether phase was washed with 1N HCl, water, and saturated sodium bicarbonate, then dried over magnesium sulfate. Filtration and evaporation of solvent gave the crude product that was purified by flash chromatography on silica gel, eluting with 2% methanol/dichloromethane. N-cyano-(D)-prolyl-leucine benzyl ester (11) was isolated as a pale yellow oil.

$^1$H NMR (300 MHz, DMSO-d6): δ 8.52 (d, J=8 Hz, 1H), δ 7.35 (bs, 5H), δ 5.11 (s, 2H), δ 4.34 (m, 1H), δ 4.13 (m, 1H), δ 3.48 (m, 1H), δ 3.38 (m, 1H), δ 1.51–1.83 (m, 6H), δ 0.85 (m, 6H).

$^{13}$C APT NMR (67.5 MHz, CDCl$_3$): δ 172.4 (e), 170.0 (e), 135.2 (e), 128.7 (o), 128.6 (o), 128.4 (o), 116.4 (e), 67.3 (e), 65.3 (o), 52.7 (e), 50.9 (o), 41.1 (e), 31.2 (e), 24.9 (o), 24.5 (c), 22.9 (o), 21.7 (o). MS (electrospray): mH$^+$344 (100%).

To a stirred solution of the amide (12) (1.43 g, 1 equiv.) in CH$_3$CN (30 mL) was added Cs$_2$CO$_3$ (3.25 g, 1 equiv.) and the suspension was stirred at rt for 1 h. A solution of BrCN in CH$_2$Cl$_2$ (1 M, 15 mL, 1.5 equiv.) was added and the resultant suspension was stirred at rt for 16 h. Since the reaction had not proceeded to completion, an additional aliquot of BrCN in CH$_2$Cl$_2$ (1 M, 10 mL, 1 equiv.) was added and the resultant suspension was stirred at rt for an additional 48 h. The suspension was filtered off and washed with CH$_2$Cl$_2$. The filtrate was washed with H$_2$O and brine, dried (MgSO$_4$) and concentrated under reduced pressure. The resultant residue was purified by flash chromatography (gradient elution: 30% EtOAc in hexane to 50% EtOAc in hexane) to afford the desired methyl 1-cyano-5-oxo-2-pyrrolidinecarboxylate (13).

$^1$H NMR (300 MHz, acetone-d6): δ 4.89 (m, 1H), 3.81 (s, 3H), 2.30–2.75 (m, 4H).

SCHEME 3

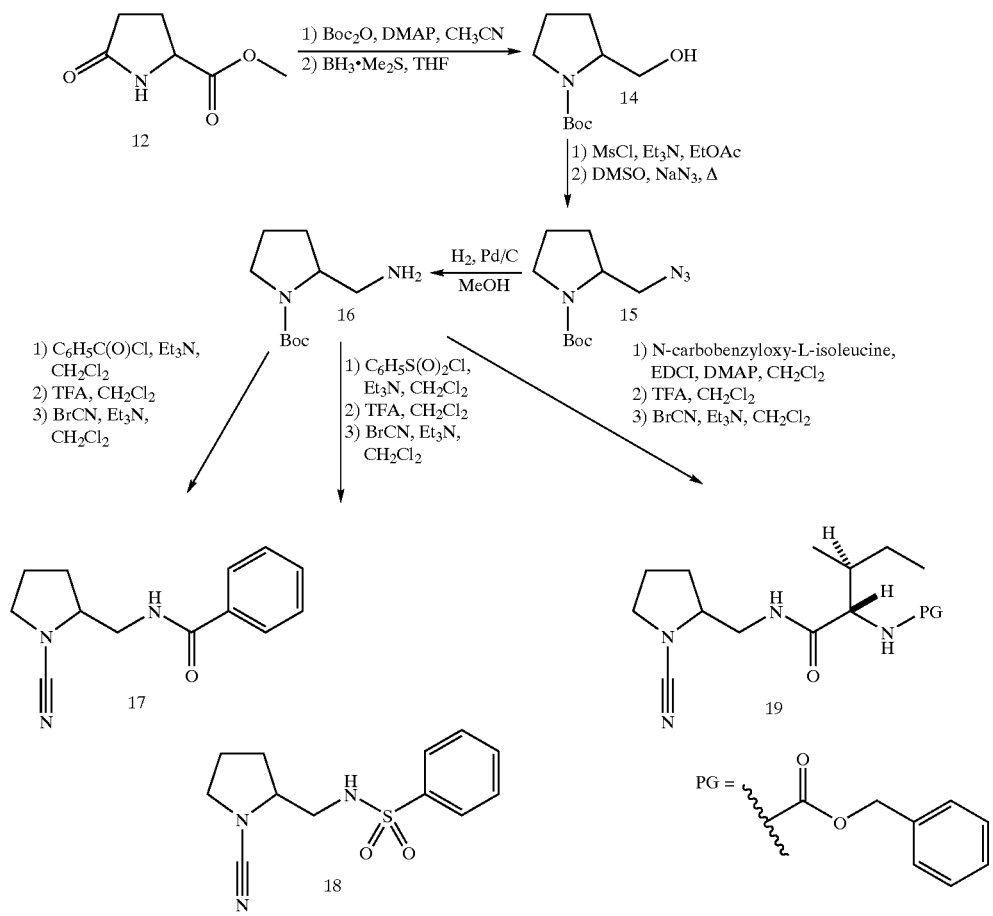

Following general procedure 1, to a solution of the amide (12) (53 g, 1 equiv.) in $CH_3CN$ (250 mL) was added a solution of DMAP (42 g, 0.9 equiv.) in $CH_3CN$ (100 mL) followed by the dropwise addition (over 30 minutes) of $Boc_2O$ (81 g, 1 equiv.) in $CH_3CN$ (100 mL). The resultant solution was stirred at rt for 3 h followed by the addition of an additional aliquot of $Boc_2O$ (45 g, 0.5 equiv.). The mixture was stirred for an additional 16 h at rt followed by the work-up procedure described in general procedure 1 to yield the desired Boc-protected amide. To a stirred solution of this Boc-protected amide (48 g, 1 equiv.) in TBF (200 mL) was added, dropwise, a solution of $BH_3.Me_2S$ in THF (2 M, 190 mL, 2 equiv.). The resultant mixture was then heated to reflux for 1 h. The reaction was cooled to rt and MeOH was added (30 mL). The solution was concentrated under reduced pressure and the residue was then dissolved in EtOAc, washed with sat. aq. $NH_4Cl$ (2×) and brine. The organic extract was dried ($MgSO_4$) and concentrated under reduced pressure to afford an oil which was purified by flash chromatography to yield the alcohol (14).

Following general procedure 4, to a cold (0° C.), stirred solution of the alcohol (14) (8.82 g, 1 equiv.) in EtOAc (120 mL) was added $Et_3N$ (8.69 mL, 1.5 equiv.) followed by MsCl (3.85 mL, 1.2 equiv.). The resultant suspension was stirred at rt for 0.5 h. The undissolved material ($Et_3N$—HCl) was filtered off and washed with EtOAc. The organic filtrate was concentrated under reduced pressure to afford an oil. This crude oil (mesylate) was dissolved in DMSO (80 mL) and $NaN_3$ (4.05 g, 1.5 equiv.) was added. The resultant reaction mixture was stirred at 70° C. for 2 hours. The reaction mixture was then poured into $H_2O$ and extracted with $Et_2O$ (4×). The combined organic extracts were washed with $H_2O$ and brine, dried over $MgSO_4$ and concentrated under reduced pressure to afford a residue which was purified by flash chromatography (25% EtOAc in hexane) to yield the desired azide (15).

To a stirred solution of the azide (15) (6.75 g, 1 equiv.) in MeOH (68 mL) was added 5% Pd on carbon (1 g, 15%). The solution was evacuated, placed under a $H_2$ atmosphere (1 atm) and stirred at rt for 3 days. The suspension was then filtered through celite and washed with MeOH. The filtrate was concentrated under reduced pressure to afford the desired primary amine (16).

Following general procedure 10, to a stirred solution of the amine (16) (200 mg, 1 equiv.) and $Et_3N$ (0.21 mL, 1.5 equiv.) in $CH_2Cl_2$ (5 mL) was added benzoyl bromide (0.13 mL, 1.1 equiv.). The resultant mixture was stirred at rt for 30 minutes. The mixture was then diluted with EtOAc and washed successively with 10% citric acid, $H_2O$ and brine. The organic extract was dried ($MgSO_4$) and concentrated under reduced pressure. The residue was purified by flash chromatography (gradient elution: 10% EtOAc in hexane to 33% EtOAc in hexane) to afford the desired coupled product. The N-Boc group of the coupled product was then converted to the cyanamide (N—CN) following general procedure 3 (i.e. successive treatment with TFA and BrCN). The crude material was purified by flash chromatography (gradient elution: 50% EtOAc in hexane to 67% EtOAc in hexane) to afford the desired N-[(1-cyano-2-pyrrolidinyl)methyl]benzamide (17).

$^1$H NMR (500 MHz, $CDCl_3$): δ 7.67 (d, 2H), 7.35 (m, 3H), 6.45 (br s, 1H), 3.72 (m, 2H), 3.37 (m, 3H), 1.96 (m, 1H), 1.70 (m, 21), 1.60 (m, 1H).

Following general procedure 11, to a stirred solution of the amine (16) (200 mg, 1 equiv.) and $Et_3N$ (0.21 mL, 1.5 equiv.) in $CH_2Cl_2$ (5 mL) was added benzenesulfonyl chloride (0.14 mL, 1.1 equiv.). The resultant mixture was stirred at rt for 30 minutes. The mixture was then diluted with EtOAc and washed successively with 10% citric acid, $H_2O$ and brine. The organic extract was dried ($MgSO_4$) and concentrated under reduced pressure. The residue was purified by flash chromatography (gradient elution: 10% EtOAc in hexane to 33% EtOAc in hexane) to afford the desired coupled product (350 mg, 103% yield). The N-Boc group of the coupled product was then converted to the cyanamide (N—CN) following general procedure 3 (i.e. successive treatment with TFA and BrCN). The crude material was purified by flash chromatography (gradient elution: 50% EtOAc in hexane to 67% EtOAc in hexane) to afford the desired N-[(1-cyano-2-pyrrolidinyl)methyl]benzenesulfonanmide (18).

$^1$H NMR (500 MHz, $CDCl_3$): δ 7.76 (d, 2H), 7.48 (m, 3H), 4.70 (br t, 1H), 3.58 (m, 1H), 3.30 (m, 2H), 3.02 (m, 2H), 1.82 (m, 4H).

Following general procedure 9, to a stirred solution of the amine (16) (200 mg, 1 equiv.), N-carbobenzyloxy-L-isoleucine (265 mg, 1 equiv.) and EDCI (211 mg, 1.1 equiv.) in $CH_2Cl_2$ (5 mL) was added DMAP (61 mg, 0.5 equiv.). The resultant mixture was stirred at rt for 16 h. The mixture was then diluted with EtOAc and washed successively with 10% citric acid, $H_2O$ and brine. The organic extract was dried ($MgSO_4$) and concentrated under reduced pressure. The residue was purified by flash chromatography (gradient elution: 25% EtOAc in hexane to 50% EtOAc in hexane) to afford the desired coupled product. The N-Boc group of the coupled product was then converted to the cyanamide (N—CN) following general procedure 3 (i.e. successive treatment with TFA and BrCN). The crude material was purified by flash chromatography (gradient elution: 50% EtOAc in hexane to 75%

EtOAc in hexane) to afford the desired solid benzyl (1S,2S)-1-({[(1-cyano-2-pyrrolidinyl)methyl]amino}carbonyl)-2-methylbutylcarbamate (19).

$^1$H NMR (300 MHz, $CDCl_3$): δ 7.32 (br s, 5H), 6.60 (m, 1H), 5.40 (in, 1H), 5.09 (d, 2H), 4.04 (m, 2H), 3.67 (m, 1H), 3.37 (m, 3H), 1.89 (m, 4H), 1.52 (m, 2H), 1.10 (m, 1H), 0.87 (t, 6H).

SCHEME 4

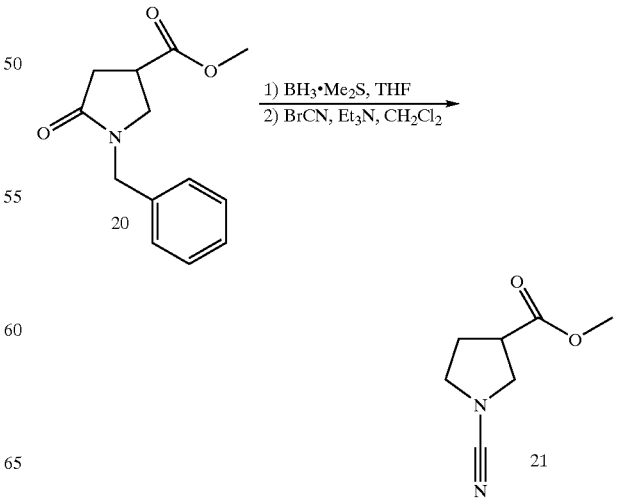

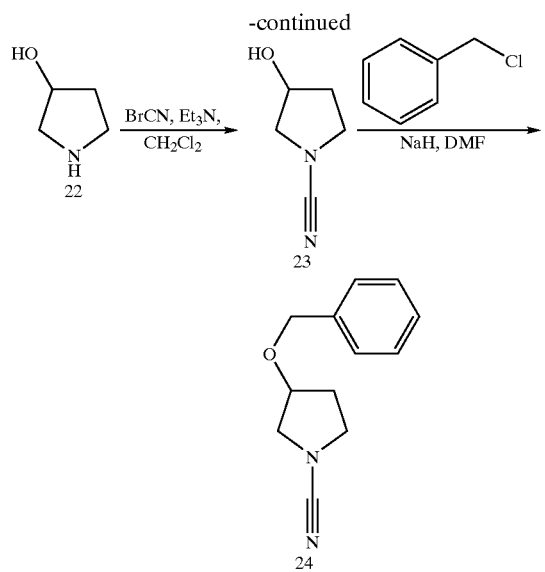

Following general procedure 5, to a cold (0° C.), stirred solution of amide (20) (32.7 g, 1 equiv.) in THF (70 mL) was added, dropwise, a solution of BH$_3$-Me$_2$S in THF (2 M, 140 mL, 2 equiv.). The resultant mixture was then heated to reflux for 2 h. The reaction was cooled to 0° C. and MeOH was added (25 mL). This mixture was stirred under reflux for 3 h and then cooled to rt. The solution was concentrated under reduced pressure and to the resultant residue was added ice (30 g) and 10 N NaOH until the pH of the mixture was adjusted to pH 9. The mixture was then extracted with CH$_2$Cl$_2$ (2×), dried (MgSO$_4$) and concentrated under reduced pressure to afford the desired benzyl amine which was purified by distillation (bp 125–135° C., 1–2 mm Hg) of the benzyl amine. To a solution of the benzyl amine (219 mg, 1 equiv.) in CH$_2$Cl$_2$ (5 mL) was added a solution of BrCN in CH$_2$Cl$_2$ (1 M, 1.5 mL, 1.5 equiv.). The mixture was refluxed for 30 min, cooled to rt and concentrated under reduced pressure. The resultant residue was purified by flash chromatography (gradient elution 20% EtOAc in hexane to 50% EtOAc in hexane) to afford the desired methyl 1-cyano-3-pyrrolidinecarboxylate (21).

$^1$H NMR (400 MHz, CDCl$_3$): δ 3.74 (s, 3H), 3.60 (m, 2H), 3.45 (m, 2H), 3.10 (m, 1H), 2.15 (m, 2H).

To a cold (0° C.), stirred solution of 3-pyrrolidinol (22) (181 mg, 1 equiv.) in CH$_2$Cl$_2$ (20 mL) was added Et$_3$N (0.73 mL, 2.5 equiv.) followed by a solution of BrCN in CH$_2$Cl$_2$ (1 M, 2.5 mL, 1.2 equiv.). The resultant reaction mixture was stirred at 0° C. for 2 h. The solution was warmed to rt, diluted with EtOAc and washed with H$_2$O and brine. The organic extract was dried (MgSO$_4$), concentrated under reduced pressure and the resultant residue was purified by flash chromatography (gradient elution: 100% EtOAc to 50% MeOH in EtOAc) to afford the desired 1-cyano-3-pyrrolidinol (23).

$^1$H NMR (400 MHz, MeOH-d4): δ 4.38 (m, 1H), 3.52 (m, 3H), 3.25 (dt, 1H), 1.95 (m, 2H); m/z (+APCI): 113.0 (M+1)$^+$.

Following general procedure 12, to a cold (0° C.), stirred solution of the alcohol (23) (58 mg, 1 equiv.) in DMF (5 mL) was added NaH (60% in oil, 31 mg, 1.5 equiv.). The suspension was stirred at 0° C. for 40 minutes followed by the addition of the benzyl chloride (120 uL, 2 equiv.). The suspension was warmed to rt and stirred for 6 h. MeOH was added followed by sat. aq. NH$_4$Cl. The aqueous phase was extracted with EtOAc (3×) and the combined organic extracts were washed with brine, dried (MgSO$_4$) and concentrated under reduced pressure. The residue was purified by flash chromatography (25% EtOAc in hexane) to afford the desired benzyl ether 3-(benzyloxy)-1-cyanopyrrolidine (24).

$^1$H NMR (400 MHz, acetone-d6): δ 7.30 (m, 5H), 4.56 (s, 2H), 4.25 (m, 1H), 3.46 (m, 4H), 2.13 (m, 1H), 2.03 (m, 1H); m/z (+APCI): 203.1 (M+1)$^+$.

SCHEME 5

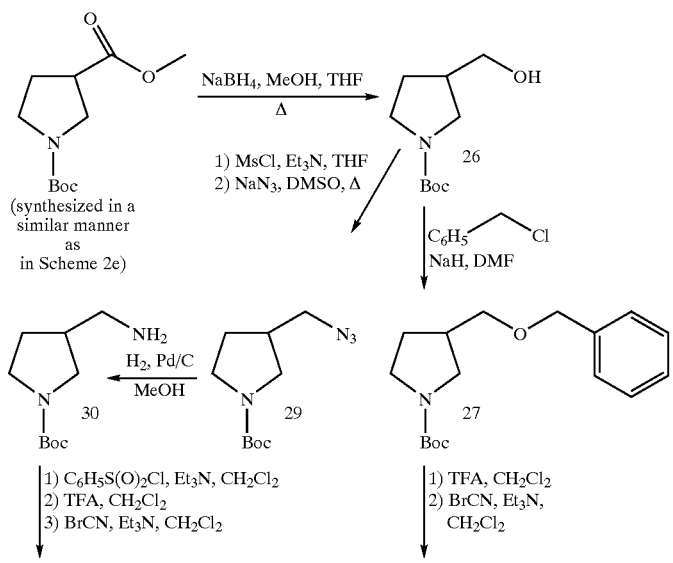

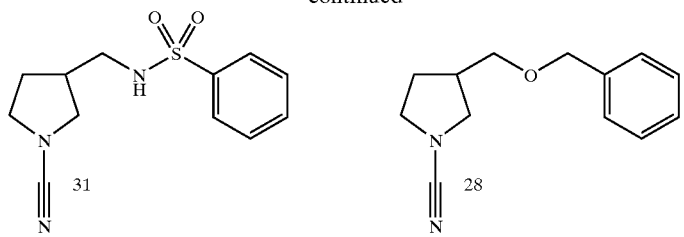

Following general procedure 6, to a refluxing suspension of the ester (25) (2.29 g, 1 equiv.) and NaBH$_4$ (757 mg, 2 equiv.) in THF (10 mL) was added, dropwise, MeOH (2 mL). After the addition of MeOH, the resulting mixture was refluxed for 1 h. The mixture was then poured into 10% citric acid and extracted with EtOAc (3×). The combined organic extracts were washed with H$_2$O and brine, dried (MgSO$_4$) and concentrated under reduced pressure. The resultant oil was purified using flash chromatography (gradient elution: 50% EtOAc in hexane to 70% EtOAc in hexane) to afford the desired alcohol (26).

Following general procedure 12, to a cold (0° C.), stirred solution of the alcohol (26) (188 mg, 1 equiv.) in DMF (9 mL) was added NaH (60% in oil, 56 mg, 1.5 equiv.). The suspension was stirred at 0° C. for 40 minutes followed by the addition of the benzyl chloride (215 uL, 2 equiv.). The suspension was warmed to rt and stirred for 16 h. MeOH was added followed by sat. aq. NH$_4$Cl. The aqueous phase was extracted with EtOAc (3×) and the combined organic extracts were washed with brine, dried (MgSO$_4$) and concentrated under reduced pressure. The residue was purified by flash chromatography (20% EtOAc in hexane) to afford the desired benzyl ether (27). The N-Boc group of the benzyl ether (27) was then converted to the cyanamide (N—CN) following general procedure 3 (i.e. successive treatment with TFA and BrCN). The crude material was purified by flash chromatography (gradient elution: 30% EtOAc in hexane to 50% EtOAc in hexane) to afford the desired product 3-[(benzyloxy)methyl]-1-cyanopyrrolidine (28).

$^1$H NMR (400 MHz, acetone-d6): δ 7.30 (m, 5H), 4.53 (s, 2H), 3.43 (m, 5H), 3.18 (dd, 1H), 2.59 (m, 11), 2.03 (m, 1H), 1.74 (m, 1H); m/z (+APCI): 217.1 (M+1)$^+$.

Following general procedure 4, to a cold (0° C.), stirred solution of the alcohol (26) (250 mg, 1 equiv.) in THF (25 mL) was added Et$_3$N (346 uL, 2 equiv.) followed by MsCl (144 uL, 1.5 equiv.). The resultant suspension was stirred at rt for 40 min. The suspension was then diluted with EtOAc and the mixture was washed with 10% citric acid, H$_2$O, sat. aq. NaHCO$_3$ and brine. The combined aqueous washings were back extracted with EtOAc (3×) and the combined organic extracts were dried over MgSO$_4$ and concentrated under reduced pressure to afford the desired mesylate which was used immediately in the next reaction. This crude oil (mesylate) was dissolved in DMSO (3 mL) and NaN$_3$ (173 mg, 2 equiv.) was added. The resultant reaction mixture was stirred at 100° C. for 5 hours. The reaction mixture was then poured into H$_2$O and extracted with Et$_2$O (4×). The combined organic extracts were washed with H$_2$O and brine, dried over MgSO$_4$ and concentrated under reduced pressure to afford the crude azide (29).

To a stirred solution of the crude azide (29) (295 mg, 1 equiv.) in MeOH/CHCl$_3$ (2 mL each) was added 10% Pd on carbon (30 mg, 10%). The solution was evacuated, placed under a H$_2$ atmosphere (1 atm) and stirred at rt for 16 h. The suspension was then filtered through celite and washed with MeOH. The filtrate was concentrated under reduced pressure to afford the desired primary amine (30).

Following general procedure 11, to a stirred solution of the amine (30) (109 mg, 1 equiv.) and Et$_3$N (130 uL, 1.7 equiv.) in CH$_2$Cl$_2$ (7 mL) was added benzenesulfonyl chloride (97 uL, 1.4 equiv.). The resultant mixture was stirred at rt for 16 h. The mixture was then diluted with EtOAc and washed successively with 10% citric acid, H$_2$O and brine. The organic extract was dried (MgSO$_4$) and concentrated under reduced pressure. The residue was purified by flash chromatography (50% EtOAc in hexane) to afford the desired coupled product. The N-Boc group of the coupled product was then converted to the cyanamide (N—CN) following general procedure 3 (i.e. successive treatment with TFA and BrCN). The crude material was purified by flash chromatography (50% EtOAc in hexane) to afford the desired N-[(1-cyano-3-pyrrolidinyl)methyl]benzenesulfonamide (31).

$^1$H NMR (400 MHz, acetone-d6): δ 7.88 (m, 2H), 7.62 (m, 3H), 6.68 (br s, 1H), 3.38 (m, 3H), 3.12 (dd, 1H), 2.97 (t, 2H), 2.46 (m, 1H), 2.02 (m, 1H), 1.70 (m, 1H); m/z (+APCI): 266.0 (M+1)$^+$.

SCHEME 6

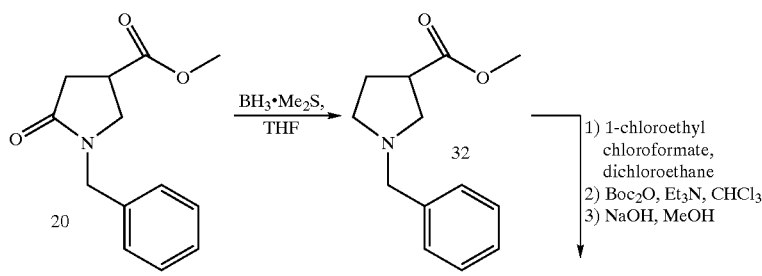

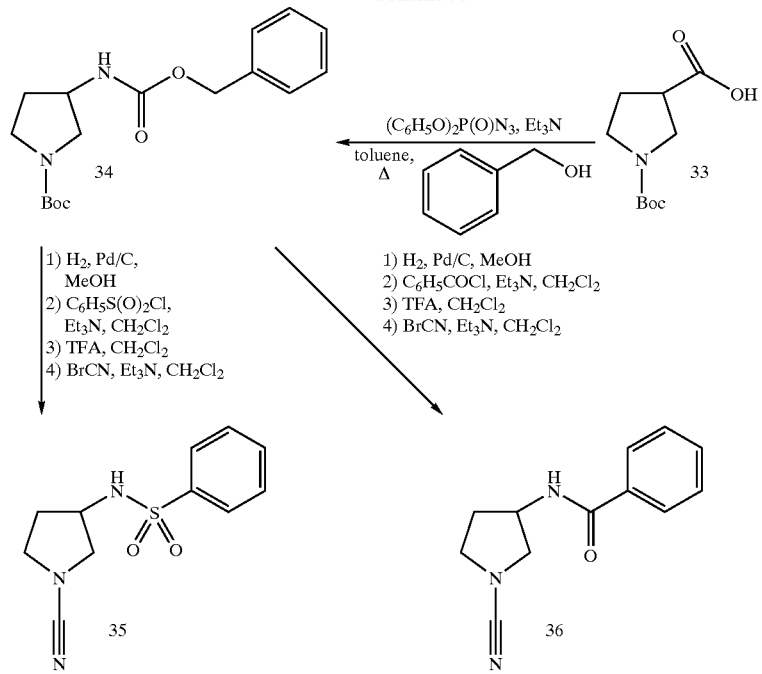

Following general procedure 5, to a cold (0° C.), stirred solution of amide 20 (32.7 g, 1 equiv.) in TBF (70 mL) was added, dropwise, a solution of BH$_3$.Me$_2$S in TBF (2 M, 140 mL, 2 equiv.). The resultant mixture was then heated to reflux for 2 h. The reaction was cooled to 0° C. and MeOH was added (25 mL). This mixture was stirred under reflux for 3 h and then cooled to rt. The solution was concentrated under reduced pressure and to the resultant residue was added ice (30 g) and 10 N NaOH until the pH of the mixture was adjusted to pH 9. The mixture was then extracted with CH$_2$Cl$_2$ (2×), dried (MgSO$_4$) and concentrated under reduced pressure to afford the desired amine which was purified by distillation (bp 125–135° C., 1–2 mm Hg) to yield the benzyl amine (32).

To a stirred solution of the benzyl amine (32) (10 g, 1 equiv.) in dichloroethane (220 mL) was added, dropwise, 1-chloroethylchloroformate (5.91 mL, 1.2 equiv.). The reaction was stirred at rt for 30 min followed by concentration of the mixture under reduced pressure. The residue was dissolved in MeOH (100 mL), refluxed for 20 min and then concentrated under reduced pressure. The residue was then dissolved in CHCl$_3$ (80 mL) and Et$_3$N (19.1 mL, 3 equiv.) and cooled to 0° C. To this mixture was added Boc$_2$O (9.95 g, 1 equiv.) in CHCl$_3$ (20 mL) and the reaction was stirred at rt for 16 h. This mixture was then concentrated under reduced pressure, dissolved in EtOAc and washed with 10% citric acid, H$_2$O and brine. The organic extract was dried (MgSO$_4$) and concentrated under reduced pressure. The residue was purified by flash chromatography (gradient elution: 20% EtOAc in hexane to 33% EtOAc in hexane) to afford the Boc-protected amine. To a solution of the Boc-protected amine (2.29 g, 1 equiv.) in MeOH (24 mL) was added 1 N NaOH (12 mL, 1.2 equiv.). The mixture was stirred at rt for 3 days and then concentrated under reduced pressure. The residue was poured into a solution of 1 N HCl (10 mL) and 10% citric acid (20 mL). The mixture was extracted with EtOAc (3×) and the combined organic extracts were washed with H$_2$O and brine, dried (MgSO$_4$) and concentrated under reduced pressure to yield the acid (33).

Following general procedure 7, to a stirred solution of the acid (33) (1.505 g, 1 equiv.) and Et$_3$N (1.17 mL, 1.2 equiv.) in toluene (20 mL) was added DPPA (1.66 mL, 1.1 equiv.). After stirring at rt for 10 minutes, the mixture was refluxed for 1 h. To this refluxing mixture was added benzyl alcohol (1.45 mL, 2 equiv.) and the refluxing was continued for 14 h. The resultant mixture was poured into 1 N aq. NaOH and extracted with Et$_2$O (3×). The combined organic extracts were washed successively with H$_2$O, 10% citric acid, H$_2$O and brine. The organic extracts were dried (MgSO$_4$), concentrated under reduced pressure and the residue was purified by flash chromatography (gradient elution: 20% EtOAc in hexane to 67% EtOAc in hexane) to afford the benzyl carbamate intermediate (34).

To a stirred solution of the benzyl carbamate intermediate (34) (1.95 g, 1 equiv.) in MeOH (20 mL) was added 10% palladium on carbon (200 mg, 10%). The solution was evacuated, placed under a H$_2$ atmosphere (35 atm) and shaken for 5 h. The suspension was then filtered through celite and washed with MeOH. The filtrate was concentrated under reduced pressure to afford the desired amine. Following general procedure 11, to a stirred solution of this amine (100 mg, 1 equiv.) and Et$_3$N (120 uL, 1.6 equiv.) in CH$_2$Cl$_2$ (5 mL) was added benzenesulfonyl chloride (82 uL, 1.2 equiv.). The resultant mixture was stirred at rt for 16 h. The mixture was then diluted with EtOAc and washed successively with 10% citric acid, H$_2$O and brine. The organic extract was dried (MgSO$_4$) and concentrated under reduced pressure. The residue was purified by flash chromatography (gradient elution: 10% EtOAc in hexane to 67% EtOAc in hexane) to afford the desired coupled product. The N-Boc group of the coupled product was then converted to the cyanamide (N—CN) following general procedure 3 (i.e. successive treatment with TFA and BrCN). The crude material was purified by flash chromatography (gradient elution: 33% EtOAc in hexane to 70% EtOAc in hexane) to afford the desired N-(1-cyano-3-pyrrolidinyl)benzenesulfonamide (35).

$^1$H NMR (500 M, CDCl$_3$): δ 7.78 (d, 2H), 7.53 (m, 1H), 7.43 (in, 2H), 4.90 (d, 1H), 3.79 (in, 1H), 3.32 (m, 3H), 3.03 (m, 1H), 1.95 (m, 1H), 1.73 (m, 1H); m/z (+APCI): 251.9 (M+1)$^+$.

To a stirred solution of the benzyl carbamate intermediate (34) (1.95 g, 1 equiv.) in MeOH (20 mL) was added palladium on carbon (200 mg, 10%). The solution was evacuated, placed under a H₂ atmosphere (35 atm) and shaken for 5 h. The suspension was then filtered through celite and washed with MeOH. The filtrate was concentrated under reduced pressure to afford the desired amine. Following general procedure 10, to a stirred solution of this amine (105 mg, 1 equiv.) and Et₃N (160 uL, 2 equiv.) in CH₂Cl₂ (5 mL) was added benzoyl bromide (90 uL, 1.3 equiv.). The resultant mixture was stirred at rt for 10 min. The mixture was concentrated under reduced pressure and the residue was purified by flash chromatography (50% EtOAc in hexane) to afford the desired coupled product. The N-Boc group of the coupled product was then converted to the cyanamide (N—CN) following general procedure 3 (i.e. successive treatment with TFA and BrCN). The crude material was purified by flash chromatography (gradient elution: 50% EtOAc in hexane to 67% EtOAc in hexane) to afford the desired cyanamide N-(1-cyano-3-pyrrolidinyl) benzamide (36).

¹H NMR (300 MHz, CDCl₃): δ 7.76 (d, 2H), 7.47 (m, 31H), 6.23 (m, 1H), 4.70 (m, 1H), 3.75 (dd, 1H), 3.57 (m, 2H), 3.39 (dd, 1H), 2.30 (m, 1H), 2.03 (m, 1H); m/z (+APCI): 216.1 (M+1)⁺.

To the a stirred solution of the epoxide (38) (180 mg, 1 equiv.) in MeOH/H₂O (8:1 mixture, 5 mL) was added NH₄Cl (114 mg, 2.2 equiv.) followed by NaN₃ (316 mg, 5 equiv.). The solution was heated to 70° C. for 17 h. After cooling to rt, Et₂O and sat. aq. NaHCO₃ were added and the aqueous extract was extracted with Et₂O (2x) and EtOAc (2x). The combined organic extracts were washed with brine, dried (MgSO₄) and concentrated under reduced pressure. The resultant residue was purified by flash chromatography (gradient elution: 35% EtOAc in hexane to 50% EtOAc in hexane) to afford the azide (39).

To a stirred solution of the azide (39) (86 mg, 1 equiv.) in MeOH/CHCl₃ (2 mL each) was added 10% palladium on carbon (10 mg, 9%). The solution was evacuated, placed under a H₂ atmosphere (1 atm) and stirred for 48 h. The suspension was then filtered through celite and washed with MeOH. The filtrate was concentrated under reduced pressure to afford the desired amine. Following general procedure 11, to a stirred solution of this amine (76 mg, 1 equiv.) and Et₃N (73 uL, 1.4 equiv.) in CH₂Cl₂ (4 mL) was added benzenesulfonyl chloride (58 uL, 1.2 equiv.). The resultant mixture was stirred at rt for 4 h. The mixture was then diluted with EtOAc and washed successively with 10% citric acid, H₂O and brine. The organic extract was dried (MgSO₄) and concentrated under reduced pressure. The residue was purified by flash chromatography (gradient elution: 50% EtOAc in hexane to 100% EtOAc) to afford the desired coupled product (40).

Following general procedure 12, to a cold (0° C.), stirred solution of the alcohol (40) (92 mg, 1 equiv.) in DMF (3 mL)

SCHEME 7

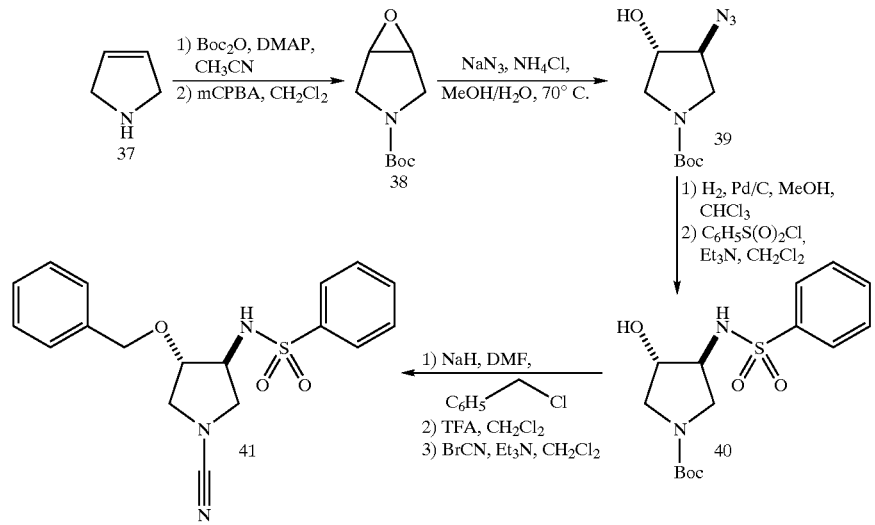

Following general procedure 1, to a cold (0° C.) solution of the 3-pyrroline (37) (1 g, 1 equiv.) in CH₃CN (20 mL) was added DMAP (3.53 g, 2 equiv.) followed by the dropwise addition (over 30 minutes) of Boc₂O (3.8 g, 1.2 equiv.) in CH₃CN (10 mL). The resultant solution was stirred at rt for 24 h. The mixture was diluted with EtOAc, washed with 10% citric acid, H₂O and brine. The organic extract was dried (MgSO₄) and concentrated under reduced pressure to afford the desired Boc-protected amine. To a cold (0° C.), stirred solution of this Boc-protected amine (2.19 g, 1 equiv.) in CH₂Cl₂ (50 mL) was added mCPBA (57%, 4.7 g, 1.2 equiv.). The solution was warmed to rt and stirred for 16 h. The resultant suspension was filtered through celite and washed with hexane. The filtrate was washed with sat. aq. thiosulfate (1x), sat. aq. NaHCO₃ (2x) and brine (2x). The organic extract was dried (MgSO₄) and concentrated under reduced pressure to yield a solid residue which was purified by flash chromatography (gradient elution: 30% EtOAc in hexane to 60% EtOAc in hexane) to yield the desired epoxide (38).

was added NaH (60% in oil, 24 mg, 2.2 equiv.). The suspension was stirred at 0° C. for 1 h followed by the addition of the benzyl chloride (37 uL, 1.2 equiv.). The suspension was warmed to rt and stirred for 45 h. MeOH was added followed by sat. aq. NH₄Cl. The aqueous phase was extracted with EtOAc (3x) and the combined organic extracts were washed with brine, dried (MgSO₄) and concentrated under reduced pressure. The residue was purified by flash chromatography (30% EtOAc in hexane) to afford the desired benzyl ether. The N-Boc group of the benzyl ether was then converted to the cyanamide (N—CN) following general procedure 3 (i.e. successive treatment with TFA and BrCN). The crude material was purified by flash chromatography (40% EtOAc in hexane) to afford the desired product N-[(3S,4S)-4-(benzyloxy)-1-cyanopyrrolidinyl]benzenesulfonamide (41).

¹H NMR (300 MHz, acetone-d6): δ 7.90 (d, 2H), 7.63 (m, 3H), 7.30 (m, 5H), 7.07 (br s, 1H), 4.53 (m, 2H), 4.08 (m, 1H), 3.90 (br s, 1H), 3.64 (m, 2H), 3.41 (br d, 1H), 3.25 (dd, 1H); m/z (+APCI): 258.0 (M+1)⁺.

Scheme 8

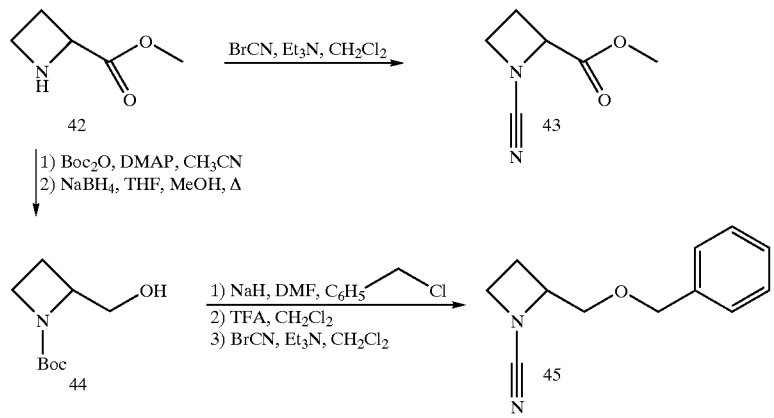

Following general procedure 3 (second reaction), the amine (42) (147mg, 1 equiv.) in CH$_2$Cl$_2$ (10 mL) was treated with Et$_3$N (0.41 mL, 3 equiv.) and BrCN (1.9 mL of a 1 M solution in CH$_2$Cl$_2$, 2 equiv.) to afford, after work-up, the desired methyl 1-cyano-2-azetidinecarboxylate (43).

$^1$H NMR (400 MHz, MeOH-d4): δ 4.95 (dd, 1H), 4.16 (m, 1H), 4.06 (m, 1H), 3.80 (s, 3H), 2.62 (m, 1H), 2.45 (m, 1H); m/z (+APCI): 141.5 (M+1)$^+$.

Following general procedure 1, to a cold (0° C.), stirred solution of the amine (42) (600 mg, 1 equiv.) in CH$_3$CN (12 mL) was added DMAP (2.9 g, 4 equiv.) followed by the dropwise addition (over 30 minutes) of Boc$_2$O (1.55 g, 1.2 equiv.) in CH$_3$CN (10 mL). The resultant solution was stirred at rt for 24 h followed by the work-up procedure described in general procedure 1. The residue was purified by flash chromatography (50% EtOAc in hexane) to yield the desired Boc-protected amine. To a refluxing suspension of the Boc-protected amine (566 mg, 1 equiv.) and NaBH$_4$ (200 mg, 2 equiv.) in THF (5 mL) was added, dropwise, MeOH (0.53 mL). After the addition of MeOH, the resulting mixture was refluxed for 1.5 h. The mixture was then poured into 10% citric acid and extracted with EtOAc (3×). The combined organic extracts were washed with H$_2$O and brine, dried (MgSO$_4$) and concentrated under reduced pressure. The resultant oil was purified by flash chromatography (gradient elution: 50% EtOAc in hexane to 100% EtOAc) to afford the desired alcohol (44).

Following general procedure 12, to a cold (0° C.), stirred solution of the alcohol (44) (100 mg, 1 equiv.) in DMF (5 mL) was added NaH (60% in oil, 32 mg, 1.5 equiv.). The suspension was stirred at 0° C. for 40 minutes followed by the addition of the benzyl chloride (125 uL, 2 equiv.). The suspension was warmed to rt and stirred for 16 h. MeOH was added followed by sat. aq. NH$_4$Cl. The aqueous phase was extracted with EtOAc (3×) and the combined organic extracts were washed with brine, dried (MgSO$_4$) and concentrated under reduced pressure. The residue was purified by flash chromatography (gradient elution: 100% hexane to 20% EtOAc in hexane) to afford the desired benzyl ether. The N-Boc group of the benzyl ether was then converted to the cyanamide (N—CN) following general procedure 3 (i.e. successive treatment with TFA and BrCN). The crude material was purified by flash chromatography (gradient elution: 30% EtOAc in hexane to 60% EtOAc in hexane) to afford the desired product 2-[(benzyloxy)methyl]-1-cyanoazetidine (45).

$^1$H NMR (400 MHz, acetone-d6): δ 7.33 (m, 5H), 4.58 (m, 3H), 4.03 (m, 2H), 3.68 (m, 2H), 2.39 (m, 1H), 2.22 (m, 1H); m/z (+APCI): 203.1 (M+1)$^+$.

SCHEME 9

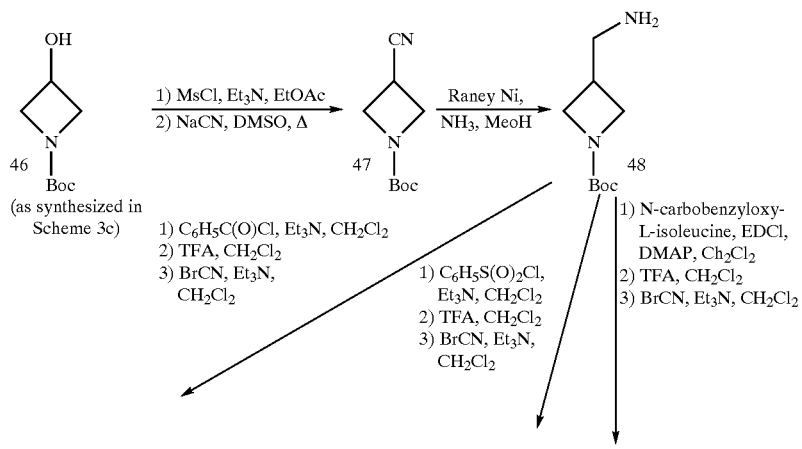

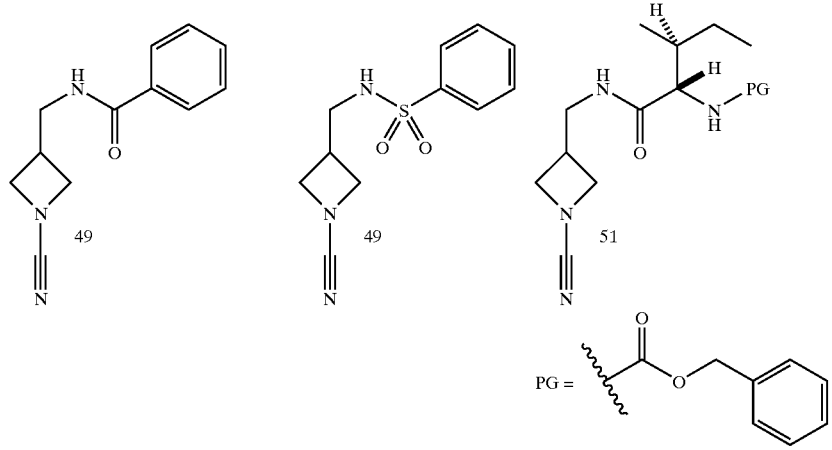

Following general procedure 4, to a cold (0° C.), stirred solution of the alcohol (46) (1.23 g, 1 equiv.) in EtOAc (10 mL) was added Et$_3$N (1.28 mL, 1.3 equiv.) followed by MsCl (0.66 mL, 1.2 equiv.). The resultant suspension was stirred at 0° C. for 1 h. The undissolved material (Et$_3$N.HCl) was filtered off and washed with EtOAc. The organic filtrate was concentrated under reduced pressure to afford an oil. This crude oil (mesylate) was dissolved in DMSO (5 mL) and NaCN (0.696 g, 2 equiv.) was added. The resultant reaction mixture was stirred at 130° C. for 2 days. The reaction mixture was then poured into H$_2$O and extracted with Et$_2$O (2×). The combined organic extracts were washed with H$_2$O and brine, dried over MgSO$_4$ and concentrated under reduced pressure to afford a residue which was purified by flash chromatography (gradient elution: 25% EtOAc in hexane to 33% EtOAc in hexane) to yield the desired nitrile (47).

To a stirred solution of the nitrile (47) (728 mg, 1 equiv.) in MeOH (5 mL) was added NH$_3$ (2M in MeOH, 10 mL) and raney nickel (1 mL). The solution was evacuated, placed under a H$_2$ atmosphere (40 atm) and stirred at rt for 3.5 h. The suspension was then filtered through celite and washed with MeOH. The filtrate was concentrated under reduced pressure to afford the desired primary amine (48).

Following general procedure 10, to a stirred solution of the amine (48) (100 mg, 1 equiv.) and Et$_3$N (0.11 mL, 1.5 equiv.) in CH$_2$Cl$_2$ (5 mL) was added benzoyl bromide (0.07 mL, 1.1 equiv.). The resultant mixture was stirred at rt for 10 minutes. The mixture was then diluted with EtOAc and washed successively with 10% citric acid, H$_2$O and brine. The organic extract was dried (MgSO$_4$) and concentrated under reduced pressure. The residue was purified by flash chromatography (gradient elution: 50% EtOAc in hexane to 70% EtOAc in hexane) to afford the desired coupled product. The N-Boc group of the coupled product was then converted to the cyanamide (N—CN) following general procedure 3 (i.e. successive treatment with TFA and BrCN). The crude material was purified by flash chromatography (gradient elution: 50% EtOAc in hexane to 67% EtOAc in hexane) to afford the desired solid N-[(1-cyano-3-azetidinyl)methyl]benzamide (49).

$^1$H NMR (500 MHz, CDCl$_3$): δ 7.65 (m, 2H), 7.38 (m, 3H), 6.34 (br s, 1H), 4.17 (m, 2H), 3.84 (m, 2H), 3.59 (m, 2H), 2.93 (m, 1H); m/z (+APCI): 216.1 (M+1)$^+$.

Following general procedure 11, to a cold (0° C.), stirred solution of the amine (48) (100 mg, 1 equiv.) and Et$_3$N (0.12 mL, 1.5 equiv.) in CH$_2$Cl$_2$ (5 mL) was added benzenesulfonyl chloride (0.08 mL, 1.1 equiv.). The resultant mixture was stirred at rt for 16 h. The mixture was then diluted with EtOAc and washed successively with 10% citric acid, H$_2$O and brine. The organic extract was dried (MgSO$_4$) and concentrated under reduced pressure. The residue was purified by flash chromatography (gradient elution: 30% EtOAc in hexane to 50% EtOAc in hexane) to afford the desired coupled product. The N-Boc group of the coupled product was then converted to the cyanamide (N—CN) following general procedure 3 (i.e. successive treatment with TFA and BrCN). The crude material was purified by flash chromatography (gradient elution: 30% EtOAc in hexane to 67% EtOAc in hexane) to afford the desired solid N-[(1-cyano-3-azetidinyl)methyl]benzenesulfonamide (50).

$^1$H NMR (400 MHz, CDCl$_3$): δ 7.85 (m, 2H), 7.58 (m, 3H), 5.20 (br t, 1H), 4.16 (t, 2H), 3.81 (dd, 2H), 3.13 (t, 2H), 2.83 (m, 1H); m/z (+APCI): 251.9 (M+1)$^+$.

Following general procedure 9, to a stirred solution of the amine (48) (186 mg, 1 equiv.), N-carbobenzyloxy-L-isoleucine (265 mg, 1 equiv.) and EDCI (211 mg, 1.1 equiv.) in CH$_2$Cl$_2$ (5 mL) was added DMAP (61 mg, 0.5 equiv.). The resultant mixture was stirred at rt for 16 h. The mixture was then diluted with EtOAc and washed successively with 10% citric acid, H$_2$O and brine. The organic extract was dried (MgSO$_4$) and concentrated under reduced pressure. The residue was purified by flash chromatography (gradient elution: 30% EtOAc in hexane to 50% EtOAc in hexane) to afford the desired coupled product. The N-Boc group of the coupled product was then converted to the cyanamide (N—CN) following general procedure 3 (i.e. successive treatment with TFA and BrCN). The crude material was purified by flash chromatography (gradient elution: 50% EtOAc in hexane) to afford the desired solid benzyl (1S, 2S)-1-({[(1-cyano-3-azetidinyl)methyl]amino}carbonyl)-2-methylbutylcarbamate (51).

$^1$H NMR (500 MHz, CDCl$_3$): δ 7.24 (m, 5H), 6.25 (br s, 1H), 5.18 (br d, 1H), 5.00 (s, 2H), 4.02 (m, 2H), 3.81 (t, 1H), 3.72 (m, 2H), 3.32 (m, 2H), 2.75 (br s, 1H), 1.79 (m, 1H), 1.38 (m, 1H), 1.01 (m, 1H), 0.80 (m, 6H); m/z (+APCI): 359.1 (M+1)$^+$.

SCHEME 10

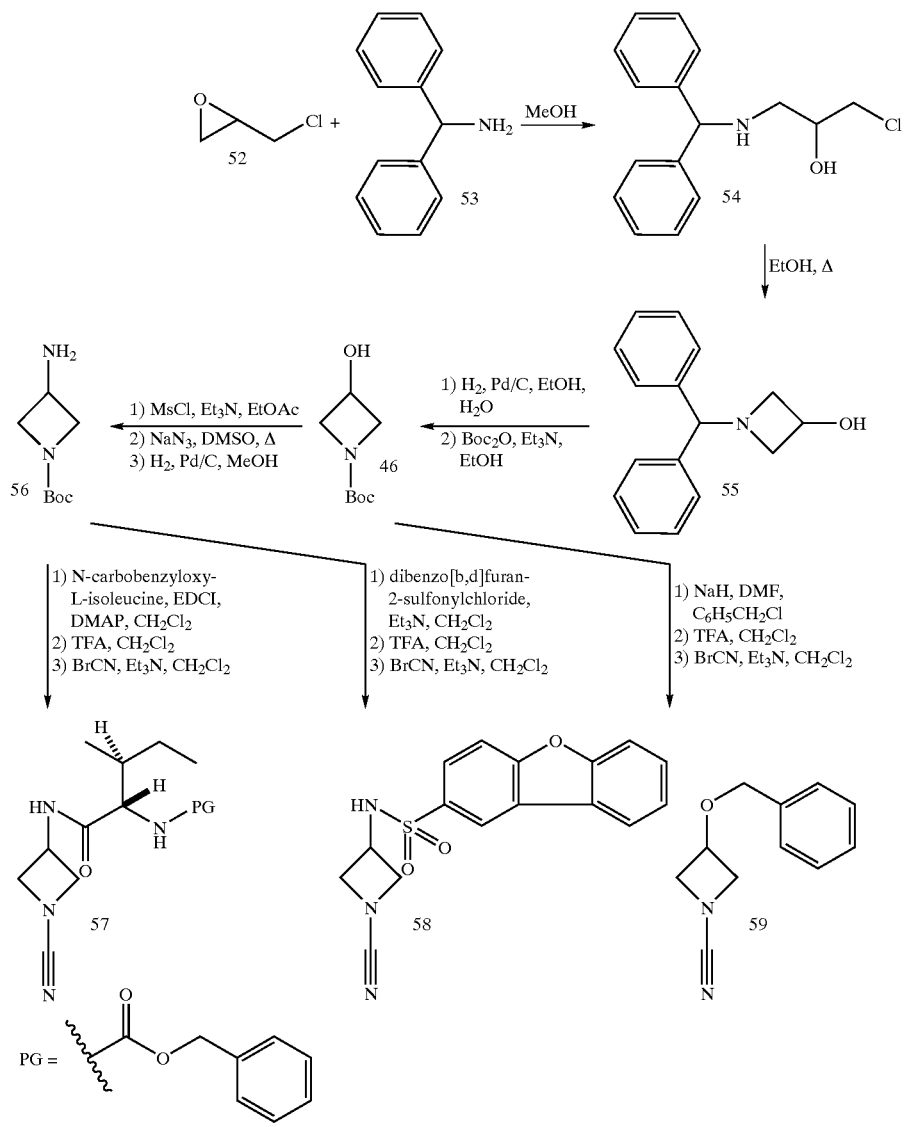

A solution of epichlorohydrin (52) (15.6 mL, 1.4 equiv.) and aminodiphenyl-methane (53) (24.6 mL, 1 equiv.) in MeOH (200 mL) was stirred at rt for 18 h to form the acyclic intermediate (54). The MeOH was removed under reduced pressure and EtOH (240 mL) was added to the residue. The mixture was heated to reflux for 3 h and then concentrated under reduced pressure. The residue was triturated with $CH_2Cl_2$ to afford a white solid which was washed with $CH_2Cl_2$ to yield the desired 4-membered ring alcohol (55).

To a stirred solution of (55) (10.6 g, 1 equiv.) in EtOH/$H_2O$ (100 and 20 mL, respectively) was added 5% Pd on carbon (1 g, 10%). The solution was evacuated, placed under a $H_2$ atmosphere (60 atm) and stirred at rt for 16 h. The suspension was then filtered through celite and washed with MeOH. The filtrate was concentrated under reduced pressure to afford the desired amine. To a cold (0° C.), stirred solution of the amine (2 g, 1 equiv.) in EtOH (35 mL) was added $Et_3N$ (7.5 mL, 2 equiv.) followed by $Boc_2O$ (6.47 g, 1.1 equiv.). The resultant solution was stirred at rt for 30 min and then concentrated under reduced pressure. The residue was diluted with EtOAc, washed with 10% citric acid, $H_2O$ and brine. The organic extract was dried over $MgSO_4$ and concentrated under reduced pressure to afford an oil which was purified by flash chromatography (gradient elution: 67% EtOAc in hexane to 100% EtOAc) to yield the Boc-protected amine (46).

Following general procedure 4, to a cold (0° C.), stirred solution of the alcohol (46) (710 mg, 1 equiv.) in EtOAc (5 mL) was added $Et_3N$ (0.74 mL, 1.3 equiv.) followed by MsCl (0.38 mL, 1.2 equiv.). The resultant suspension was stirred at rt for 1 h. The undissolved material ($Et_3N$.HCl) was filtered off and washed with EtOAc. The organic filtrate was concentrated under reduced pressure to afford an oil. This crude oil (mesylate) was dissolved in DMSO (3 mL) and $NaN_3$ (533 mg, 2 equiv.) was added. The resultant reaction mixture was stirred at 120° C. for 3 days. The reaction mixture was then poured into $H_2O$ and extracted with $Et_2O$ (4×). The combined organic extracts were washed with $H_2O$ and brine, dried over $MgSO_4$ and concentrated under reduced pressure to afford the crude azide. To a stirred solution of the crude azide (641 mg, 1 equiv.) in MeOH/$CHCl_3$ (5 mL each) was added 10% Pd on carbon (60 mg, 10%). The solution was evacuated, placed under a H₂ atmosphere (1 atm) and stirred at rt for 16 h. The suspension was then filtered through celite and washed with MeOH. The filtrate was concentrated under reduced pressure to afford the desired primary amine (56).

Following general procedure 9, to a stirred solution of the amine (56) (172 mg, 1 equiv.), N-carbobenzyloxy-L-isoleucine (265 mg, 1 equiv.) and EDCI (192 mg, 1 equiv.) in CH₂Cl₂ (5 mL) was added DMAP (24 mg, 0.2 equiv.). The resultant mixture was stirred at rt for 16 h. The mixture was then diluted with EtOAc and washed successively with 10% citric acid, H₂O and brine. The organic extract was dried (MgSO₄) and concentrated under reduced pressure. The residue was purified by flash chromatography (gradient elution: 30% EtOAc in hexane to 50% EtOAc in hexane) to afford the desired coupled product. The N-Boc group of the coupled product was then converted to the cyanamide (N—CN) following general procedure 3 (i.e. successive treatment with TFA and BrCN). The crude material was purified by flash chromatography (gradient elution: 25% EtOAc in hexane to 50% EtOAc in hexane) to afford the desired solid benzyl (1S,2S)-1-{[(1-cyano-3-azetidinyl) amino]carbonyl}-2-methylbutylcarbamate (57).

¹H NMR (500 MHz, DMSO-d6): δ 8.73 (d, 1H), 8.61 (d, 1H), 7.32 (m, 5H), 5.90 (s, 1H), 5.01 (br s, 2H), 4.34 (m, 1H), 3.65 (m, 4H), 1.70 (m, 1H), 1.40 (m, 1H), 1.11 (m, 1H), 0.80 (m, 6H); m/z (+APCI): 345.1 (M+1)⁺.

Following general procedure 11, to a stirred solution of the amine (56) (256 mg, 1 equiv.) and Et₃N (0.31 mL, 1.5 equiv.) in CH₂Cl₂ (5 mL) was added dibenzo[b,d]furan-2-sulfonyl chloride (356 mg, 0.9 equiv.). The resultant mixture was stirred at rt for 30 min. The mixture was then diluted with EtOAc and washed successively with 10% citric acid, H₂O and brine. The organic extract was dried (MgSO₄) and concentrated under reduced pressure. The residue was purified by flash chromatography (gradient elution: 20% EtOAc in hexane to 50% EtOAc in hexane) to afford the desired coupled product. The N-Boc group of the coupled product was then converted to the cyanamide (N—CN) following general procedure 3 (i.e. successive treatment with TFA and BrCN). The crude material was washed with ether to afford the desired yellow solid N-(1-cyano-3-azetidinyl)dibenzo[b,d]furan-2-sulfonamide (58).

¹H NMR (400 MHz, acetone-d6): δ 8.64 (m, 1H), 8.28 (d, 1H), 8.02 (m, 1H), 7.85 (d, 1H), 7.75 (d, 1H), 7.63 (m, 1H), 7.46 (m, 2H), 4.40 (m, 1H), 4.24 (t, 2H), 3.95 (t, 2H); m/z (+APCI): 328.0 (M+1)⁺.

Following general procedure 12, to a cold (0° C.), stirred solution of the alcohol (46) (173 mg, 1 equiv.) in DMF (2 mL) was added NaH,(60% in oil, 60 mg, 1.5 equiv.). The suspension was stirred at 0° C. for 30 minutes followed by the addition of the benzyl chloride (230 uL, 2 equiv.). The resulting suspension was poured into H₂O and extracted with Et₂O (3×). The combined organic extracts were washed with H₂O and brine, dried (MgSO₄) and concentrated under reduced pressure. The residue was purified by flash chromatography (gradient elution: 10% EtOAc in hexane to 25% EtOAc in hexane) to afford the desired benzyl ether. The N-Boc group of the benzyl ether was then converted to the cyanamide (N—CN) following general procedure 3 (i.e. successive treatment with TFA and BrCN). The crude material was purified by flash chromatography (gradient elution: 10% EtOAc in hexane to 33% EtOAc in hexane) to afford the desired product 3-(benzyloxy)-1-cyanoazetidine (59).

¹H NMR (500 MHz, CDCl₃): δ 7.22 (m, 5H), 4.34 (s, 2H), 4.25 (m, 1H), 4.10 (m, 2H), 3.97 (m, 2H).

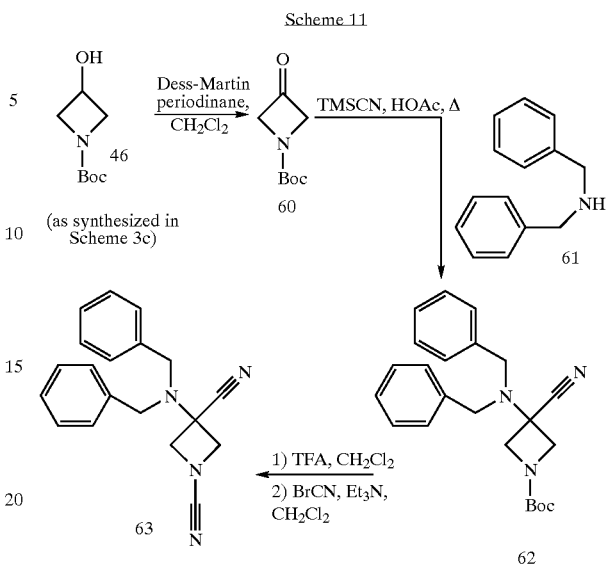

Scheme 11

To a stirred solution of the alcohol (46) (2.03 g, 1 equiv.) in CH₂Cl₂ (20 mL) was added a solution of Dess-Martin periodinane (7.47 g, 1.5 equiv.) in CH₂Cl₂ (80 mL). The mixture was stirred at rt for 1 h. The resulting suspension was filtered through a short silica plug and washed with CH₂Cl₂. The filtrate was washed with 1 N NaOH, H₂O and brine, dried (MgSO₄) and concentrated under reduced pressure to yield the desired ketone (60), as a white solid.

To a stirred solution of the ketone (60) (100 mg, 1 equiv.) and dibenzylamine (61) (0.28 mL, 2.5 equiv.) in HOAc (1 mL) was added TMSCN (0.1 mL, 1.25 equiv.). The mixture was then heated to 60° C. and stirred for 3 h. The resulting solution was poured into sat. aq. NaHCO₃ and extracted with EtOAc (3×). The organic extract was washed with H₂O and brine, dried (MgSO₄) and concentrated under reduced pressure. The residue was purified by flash chromatography (10% EtOAc in hexane) to yield the white solid (62). The N-Boc group of (62) was then converted to the cyanamide (N—CN) following general procedure 3 (i.e. successive treatment with TFA and BrCN). The crude material was purified by flash chromatography (10% EtOAc in hexane) to afford the desired product 1-cyano-3-(dibenzylamino)-3-azetidinecarbonitrile (63).

¹H NMR (400 MHz, CDCl₃): δ 7.34 (m, 10H), 3.92 (d, 2H), 3.82 (d, 2H), 3.55 (s, 4H); m/z (+APCI): 303.2 (M+1)⁺.

What is claimed is:
1. A compound of the formula:

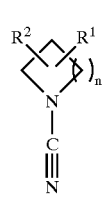

wherein
is selected from the group consisting of —(CH₂)$_p$—NH—S(O)₂—R³, —(CH₂)$_p$—NH—CO—R⁴, —(CH₂)$_p$NR⁷R⁸, —CN, —NH(CH₂)$_p$R³, —C(O)NHR⁶ and —C(O)NR⁶;

R² is selected from the group consisting of hydrogen, alkyl, oxo, —(CH₂)$_p$—NH—S(O)₂—R³, —(CH₂)$_p$—

NH—CO—R$^4$, —C(O)$_2$R$^6$, —(CH$_2$)$_p$OR$^5$, —OR$^6$, —(CH$_2$)$_p$NR$^7$R$^8$, —CN, —NH(CH$_2$)$_p$R$^3$, —(CH$_2$)$_p$R$^3$, —R$^3$, —C(O)NHR$^6$ and —C(O)NR$^6$;

R$^3$ is selected from the group consisting of aryl, arylalkyl, cycloalkyl, and heterocycloalkyl, wherein said aryl, arylalkyl and cycloalkyl groups are either unsubstituted or substituted with 1, 2 or 3 halogen atoms;

R$^4$ is selected from the group consisting of aryl, cycloalkyl, heterocycloalkyl, biaryl, CH(R$^{10}$)—NHC(O)$_2$R$^3$, OR$^5$, (CH$_2$)$_p$R$^9$, (CH$_2$)$_p$(R$^9$)$_q$, wherein said aryl, cycloalkyl, heterocycloalkyl and biaryl, groups are either unsubstituted or substituted with 1, 2 or 3 halogen atoms;

R$^5$ is selected from the group consisting of alkyl, alkenyl, alkynyl, and (CH$_2$)$_p$R$^9$;

R$^6$ is selected from the group consisting of hydrogen, alkyl, alkenyl, alkynyl, and CH(R$^{10}$)—NHC(O)$_2$R$^3$;

R$^7$ and R$^8$ are each independently selected from the group consisting of hydrogen, alkyl, alkenyl, alkynyl, and —(CH$_2$)$_p$R$^3$;

or R$^7$ and R$^8$ are joined together to form a system selected from the group consisting of aryl and heterocycloalkyl;

R$^9$ is selected from the group consisting of aryl, cycloalkyl and heterocycloalkyl;

R$^{10}$ is selected from the group consisting of the side chains of the naturally occurring amino acids or unnaturally occurring amino acids;

n is one or two;

each p is independently an integer from zero to six;

q is independently an integer from zero to four;

or a pharmaceutically acceptable salt thereof.

2. The compound according to claim 1 wherein R$^1$ is —(CH$_2$)$_p$—NH—S(O)$_2$—R$^3$ or —(CH$_2$)$_p$—NH—CO—R$^4$; and R$^2$ is selected from the group consisting of hydrogen, —(CH$_2$)$_p$—NH—S(O)$_2$—R$^3$, —(CH$_2$)$_p$—NH—CO—R$^4$, —C(O)$_2$R$^6$, —(CH$_2$)$_p$OR$^5$, —OR$^6$, —CN, —N(CH$_2$)$_p$R$^3$, —(CH$_2$)$_p$R$^3$, —C(O)NHR$^6$ and —C(O)NR$^6$.

3. The compound according to claim 2 wherein n is two.

4. The compound according to claim 3 wherein R$^{10}$ is selected from the group consisting of the side chains of leucine and isoleucine.

5. The compound according to claim 4 wherein each p is independently an integer from zero to four.

6. The compound according to claim 1 selected from the group consisting of:

N-[(1-cyano-2-pyrrolidinyl)methyl]benzamide,
N-1[(-cyano-2-pyrrolidinyl)methyl]benzenesulfonamide,
N-[(1-cyano-2-pyrrolidinyl)methyl]dibenzo[b,d]furan-2-sulfonamide,
N-(1-cyano-3-azetidinyl)dibenzo[b,d]furan-2-sulfonamide,
benzyl (1S,2S)-1-{[(1-cyano-3-azetidinyl)amino]carbonyl}-2-methylbutylcarbamate,
benzyl (1S,2S)-1-({[(1-cyano-2-pyrrolidinyl)methyl]amino}carbonyl)-2-methylbutylcarbamate,
benzyl (1S,2S)-1-({[(1-cyano-3-azetidinyl)methyl]amino}carbonyl)-2-methylbutylcarbamate,
N-[(1-cyano-3-azetidinyl)methyl]dibenzo[b,d]furan-2-sulfonamide,
benzyl 1-cyano-3-pyrrolidinylcarbamate,
N-[(1-cyano-3-azetidinyl)methyl]benzenesulfonamide,
N-[(1-cyano-3-azetidinyl)methyl]-2-naphthalenesulfonamide,
N-[(1-cyano-3-azetidinyl)methyl]benzamide,
N-(1-cyano-3-pyrrolidinyl)benzenesulfonamide,
N-[(1-cyano-3-azetidinyl)methyl]cyclohexanecarboxamide,
N-(1-cyano-3-pyrrolidinyl)[1,1'-biphenyl]-4-carboxamide,
N-(1-cyano-3-pyrrolidinyl)-2,2-diphenylacetamide,
N-(1-cyano-3-pyrrolidinyl)benzamide,
methyl (2S)-2-({[(2R)-1-cyanopyrrolidinyl]carbonyl}amino)-4-methylpentanoate,
N-(1-cyano-3-pyrrolidinyl)-4-fluorobenzenesulfonamide,
4-chloro-N-(1-cyano-3-pyrrolidinyl)benzenesulfonamide,
N-[(1-cyano-3-pyrrolidinyl)methyl]benzenesulfonamide,
benzyl (2R)-2-({[(2S)-1-cyanopyrrolidinyl]carbonyl}amino)-4-methylpentanoate,
methyl (2R)-2-({[(2S)-1-cyanopyrrolidinyl]carbonyl}amino)-4-methylpentanoate,
benzyl (1R)-1-({[(3R)-1-cyanopyrrolidinyl]amino}carbonyl)-3-methylbutylcarbamate,
benzyl (1R)-1-({[(3S)-1-cyanopyrrolidinyl]amino}carbonyl)-3-methylbutylcarbamate,
(2S)-1-cyano-N-isopentyl-2-pyrrolidinecarboxamide,
methyl (2S)-2-({[(2S,4R)-1-cyano-4-hydroxypyrrolidinyl]carbonyl}amino)-4-methylpentanoate,
(2S)-1-cyano-N-{(1S)-1-[(dimethylamino)carbonyl]-3-methylbutyl}-2-pyrrolidinecarboxamide,
N-[4-(benzyloxy)-1-cyano-3-pyrrolidinyl]benzenesulfonamide, and the pharmaceutically acceptable salts, esters and mixtures thereof.

7. A pharmaceutical composition comprising a compound according to claim 1 and a pharmaceutically acceptable carrier.

8. A pharmaceutical composition made by combining a compound according to claim 1 and a pharmaceutically acceptable carrier.

9. A process for making a pharmaceutical composition comprising combining a compound according to claim 1 and a pharmaceutically acceptable carrier.

10. A method of treating or preventing bone loss in a mammal in need thereof by administering to the mammal a therapeutically effective amount of a compound according to claim 1.

11. A method of reducing bone loss in a mammal in need thereof by administering to the mammal a therapeutically effective amount of a compound according to claim 1.

12. A method of treating or preventing bone fractures in a mammal in need thereof by administering to the mammal a therapeutically effective amount of a compound according to claim 1.

13. A method of treating or preventing osteoporosis in a mammal in need thereof by administering to the mammal a therapeutically effective amount of a compound according to claim 1.

14. A method of treating bone loss, bone fractures, osteoporosis, metastasis of melanomas, Alzheimer's disease, juvenile onset diabetes, multiple sclerosis, pemphigus vulgaris, Graves' disease, myasthenia gravis, systemic lupus erythemotasus, rheumatoid arthritis, Hashimoto's thyroiditis, allergic disorders, asthma, allogenic immune responses, refection of organ transplants or refection of tissue grafts in a mammal in need thereof by administering to the mammal a therapeutically effective amount of a compound according to claim 1.

15. A pharmaceutical composition useful for treating or preventing bone loss in a mammal comprising a pharmaceutically effective amount of a compound of claim 1 in association with a pharmaceutically acceptable carrier.

16. A pharmaceutical composition made by combining the compound of claim 1 and a pharmaceutically acceptable carrier.

* * * * *